(12) United States Patent
Dimirova et al.

(10) Patent No.: US 8,189,892 B2
(45) Date of Patent: May 29, 2012

(54) METHODS AND SYSTEMS FOR IDENTIFICATION OF DNA PATTERNS THROUGH SPECTRAL ANALYSIS

(75) Inventors: Nevenka Dimirova, Pelham Manor, NY (US); Yee Him Cheung, New York, NY (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 819 days.

(21) Appl. No.: 12/282,435

(22) PCT Filed: Mar. 7, 2007

(86) PCT No.: PCT/IB2007/050762
§ 371 (c)(1),
(2), (4) Date: Sep. 10, 2008

(87) PCT Pub. No.: WO2007/105150
PCT Pub. Date: Sep. 20, 2007

(65) Prior Publication Data
US 2009/0129647 A1    May 21, 2009

Related U.S. Application Data

(60) Provisional application No. 60/781,568, filed on Mar. 10, 2006.

(51) Int. Cl.
*G06K 9/00* (2006.01)
(52) U.S. Cl. ........................................ 382/129; 382/128
(58) Field of Classification Search .................. None
See application file for complete search history.

(56) References Cited

U.S. PATENT DOCUMENTS

| | | | |
|---|---|---|---|
| 6,054,268 | A | 4/2000 | Perlin |
| 6,287,773 | B1 | 9/2001 | Newell |
| 6,950,755 | B2 | 9/2005 | Stahl |
| 2003/0003459 | A1 | 1/2003 | Stahl |
| 2003/0097227 | A1* | 5/2003 | Bloch et al. ............... 702/75 |
| 2004/0101873 | A1 | 5/2004 | Went |
| 2009/0129647 | A1* | 5/2009 | Dimitrova et al. ......... 382/129 |

FOREIGN PATENT DOCUMENTS

WO    2004007016 A2    1/2004

OTHER PUBLICATIONS

Zhang Xin-Yu et al, "Signal Processing Techniques in Genomic Engineering" Proceedings of the IEEE vol. 90, No. 12, Dec. 2002, pp. 1822-1833.
Nath, Diganta et al "DNA_Protein Interactions: Studying the "Bendability" of DNA to Accommodate Proteins using MATLAB", Lifesciences.asu.edu. 2004.

(Continued)

*Primary Examiner* — Minh N Tang

(57) ABSTRACT

Systems and methods facilitate the location and/or identification of repetitive DNA patterns, such as CpG islands, Alu repeats, tandem repeats and various types of satellite repeats. These repetitive elements can be found within a chromosome, within a genome or across genomes of various species. The systems and methods apply image processing operators to find prominent features in the vertical and horizontal direction of the DNA spectrograms. The systems and methods for detecting and/or classifying repetitive DNA patterns include: (a) a comparative histogram method, (b) feature selection and classification using support vector machines and genetic algorithms, and (c) generation of a spectrovideo from a plurality of spectral images.

15 Claims, 18 Drawing Sheets

OTHER PUBLICATIONS

Anastassiou, Dimitris "Frequency-Domain Analysis of Biomolecular Sequences" Bioinformatics, vol. 16, No. 12, Dec. 2000, pp. 1073-1081.

Sussillo, D. et al "Spectrogram Analysis of Genomes" Eurasip Journal on Applied Signal Processing Hindawi USA, vol. 2004, No. 1, Jan. 2004, pp. 29-42.

Hall, R. et al "A Rapid Method for Illustrating Features in both Coding and Non-Coding Regions of a Genome" Bioinformatics, vol. 20, No. 6, Apr. 2004, pp. 0641-0650.

Fiers, Mark W.E.J. et al "DNAVis: Interactive Visualization of Comparative Genome Annotations" Bioinformatics Veb. 2006, vol. 22, No. 3, pp. 354-355.

* cited by examiner

AACTGGCATCCGGGAATAAGGTCT ...
$u_A[n]$ = 1100000100000110110000 ...
$u_T[n]$ = 0001000100000010000101 ...
$u_C[n]$ = 0010001001100000000010 ...
$u_G[n]$ = 0000110000111000011000 ...
FIG. 1  PRIOR ART
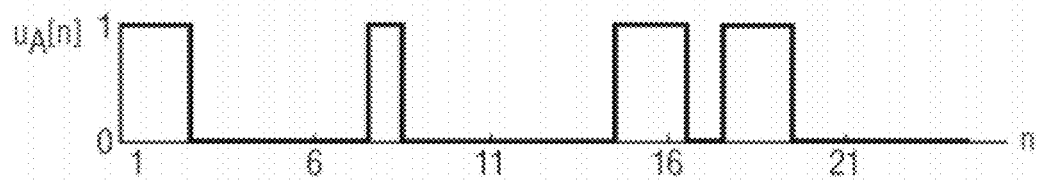
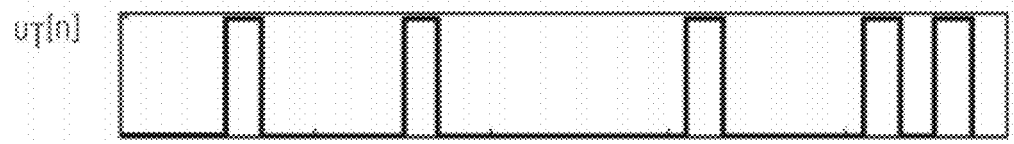
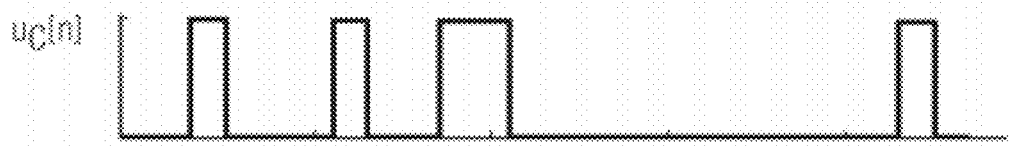
FIG. 2
PRIOR ART

Color Spectrum of the DNA segment

Color Spectrogram of a DNA sequence

METHODS AND SYSTEMS FOR IDENTIFICATION OF DNA PATTERNS THROUGH SPECTRAL ANALYSIS

BACKGROUND

1. Technical Field

The present disclosure is directed to systems and methods for facilitating DNA spectral analysis and, more particularly, to systems and methods that employ image processing techniques and/or signal processing methods to automate and/or expedite, in whole or in part, the processing of DNA sequence data. According to exemplary embodiments of the present disclosure, systems and methods are provided to support one or more of the following DNA spectral analysis techniques: (i) comparative histogram methodologies; (ii) selection/classification using support vector machines and genetic algorithms; and (iii) spectrovideo methodologies based on spectrogram extractions from DNA sequence data.

2. Background Art

Bioinformatics seeks to organize tremendous volumes of biological data into comprehensible information which can be used to derive useful knowledge. In the field of bioinformatics, techniques for spectral analysis of DNA sequences have been developed. Spectral analysis techniques generally represent an improvement over manual DNA pattern analysis techniques which aim at identifying DNA patterns serving as biological markers related to important life processes. Traditionally, automatic analyses are performed directly on strings of DNA sequences composed of the four characters A, T, C and G, which represent the four nucleotide bases. However, due to the tremendous length of DNA sequences (e.g., the length of the shortest human chromosome is 46.9 Mb), the wide range of pattern spans associated with the limited character set, and the statistical nature of the problem, such an intuitive/manual approach is inefficient, if not impossible, for achieving the desired purpose.

DNA spectral analysis offers an approach to systematically tackle the problem of deriving useful information from DNA sequence data. Generally, DNA spectral analysis involves an identification of the occurrences of each nucleotide base in a DNA sequence as an individual digital signal, and transforming each of the four nucleotide signals into a frequency domain. The magnitude of a frequency component can then be used to reveal how strongly a nucleotide base pattern is repeated at that frequency. A larger magnitude/value usually indicates a stronger presence of the repetition. To improve the readability of the results, the prior art discloses systems wherein each nucleotide base is represented by a color and the frequency spectrums of the four bases are combined and presented as a color spectrogram. These techniques are described by:

D. Anastassiou, "Frequency-Domain Analysis of Biomolecular Sequences," Bioinformatics, Vol. 16, No. 12, December 2000, pp. 1073-1081; and D. Sussillo, A. Kundaje and D. Anastassiou, "Spectrogram Analysis of Genomes," EURASIP Journal on Applied Signal Processing, Special Issue on Genomic Signal Processing, Vol. 2004, No. 1, January 2004, pp. 29-42.

The translation of the magnitudes/values for nucleotide bases into a visual image, i.e., a spectrogram, is a powerful visualization tool for DNA analysis. The resultant pixel color is indicative of the relative intensity of the four bases at a particular frequency, and the representation of DNA sequences as color images allows patterns to be more easily identified by visual inspection. In general, the hue in a spectrogram region reflects its overall nucleotide composition, and bright lines and patches in a spectrogram reveal the existence of special repetitive patterns.

An algorithm or technique for the generation of DNA spectrograms can be summarized in five steps as follows.

(i) Formation of binary indicator sequences (BISs) $u_A[n]$, $u_T[n]$, $u_C[n]$ and $u_G[n]$ for the four nucleotide bases. The BIS for a particular base takes the value of "1" at positions where the base exists and "0" otherwise. Thus, in an exemplary DNA sequence having a nucleotide sequence "AACTGGCATCCGGGAATAAGGTCT", the BIS translates as depicted in FIG. 1. Based on the foregoing exemplary DNA sequence, the BIS values may be plotted as depicted in FIG. 2.

(ii) Discrete Fourier Transform (DFT) on BISs. The frequency spectrum of each base is then obtained by computing the DFT of its corresponding BIS using Equation (1):

$$U_X[k] = \sum_{n=0}^{N-1} u_X[n]e^{-j\frac{2\pi}{N}kn}, k = 0,1,\ldots,\lfloor N/2 \rfloor + 1 \quad (1)$$

$$X = A, T, C, \text{ or } G$$

The sequence U[k] provides a measure of the frequency content at frequency k, which is equivalent to an underlying period of N/k samples as depicted in FIG. 3.

(iii) Mapping of DTF Values to RGB Colors. The four DFT sequences are reduced to three sequences in the RGB space by the following set of linear equations, collectively designated as Equation (2):

$$X_r[k] = a_r U_A[k] + t_r U_T[k] + c_r U_C[k] + g_r U_G[k]$$

$$X_g[k] = a_g U_A[k] + t_g U_T[k] + c_g U_C[k] + g_g U_G[k]$$

$$X_b[k] = a_b U_A[k] + t_b U_T[k] + c_b U_C[k] + g_b U_G[k] \quad (2)$$

where $(a_r, a_g, a_b)$, $(t_r, t_g, t_b)$, $(c_r, c_g, c_b)$ and $(g_r, g_g, g_b)$ are the color mapping vectors for the nucleotide bases A, T, C and G, respectively. The resultant pixel color $(X_r[k], X_g[k], X_b[k])$ is thus a superposition of the color mapping vectors weighted by the magnitude of the frequency component of their respective nucleotide base as depicted in FIG. 4.

FIGS. 5 and 6 further illustrate the mapping of DFT values to colors according to exemplary embodiments of the present disclosure. Thus, with reference to FIG. 5, color vectors are selected for the respective nucleotide bases A, T, C and G, respectively. In selecting color vectors, it is generally desirable to improve and/or enhance the color contrast of the DNA features. Based on exemplary color vectors, the DFT values are combined in color space, as shown in FIG. 6. Alternative mapping techniques and/or protocols may be employed, e.g., DFT values may be mapped to Hue Saturation Value (HSV space), YCrCb space, etc.

(iv) Normalizing the Pixel Values. Before rendering the color spectrograms, the RGB values of each pixel are generally normalized such that they fall between 0 and 1. There are numerous ways to implement the normalization function. The simplest approach is to divide all values by the global maximum. However, such a one-step approach may degrade the overall color contrast of the image. A better method is to perform normalization at two levels: at a first level, all pixel values are divided by a statistical maximum, e.g., equal to the overall mean plus one standard deviation, such that after the initial operation, a majority of pixels have RGB values between 0 and 1; then, at a second level, for the remaining pixels with any of their RGB values greater than one, a second level of normalization is individually performed by dividing each of such pixel values by its local maximum $\max(x_r, x_g, x_b)$. This two level approach prevents the overall intensity of the image from being excessively reduced by the more extreme pixel values and, as a result, the color contrast of the spectrogram image can be better preserved. FIG. 7 presents exemplary normalized plots of the combined DFT values of FIG. 6.

(v) Short-Time Fourier Transform (STFT). Up to now, only a single Discrete Fourier Transform (DFT) window has been considered. For long DNA sequences, however, it may be necessary to repeat steps (i) to (iv) for DFT windows that are shifted along the sequence. This results in consecutive strips of color pixels, with each of the strips depicting the frequency spectrum of a local DNA segment. A DNA spectrogram is then formed by a concatenation of these strips. The images set forth below are reproduced in FIGS. 8 and 9 hereto.

It is noted that the set of equations designated as equations (8) in the publication by D. Anastassiou ("Frequency-Domain Analysis of Biomolecular Sequences," Bioinformatics, Vol. 16, No. 12, December 2000, pp. 1073-1081) suggests that the order of steps (ii) and (iii) is reversible, i.e. it is possible to first reduce the four binary indicator sequences to three numerical sequences $(x_r, x_g, x_b)$ and then perform a Discrete Fourier Transform (DFT). This, however, needs further proof because the binary indicator sequences are not independent functions.

The appearance of a spectrogram is very much affected by the choice of the Short Term Fourier Transform (STFT) window size, the length of the overlapping sequence between adjacent windows, and the color mapping vectors. Basically, the window size determines the effective range of a pixel value in a spectrogram. A larger window results in a spectrogram that reveals statistics collected from longer DNA local segments and may be useful in identifying wider patterns. In general, the window size should be made several times larger than the length of the repetitive pattern of interest and smaller than the size of the region that contains the pattern. The window overlap determines the length of the DNA segment common to two adjacent STFT windows. Therefore, the larger the overlap, the more gradual is the transition of the frequency spectrum from one STFT window to the next. Smaller window intervals yield in higher image resolutions, thereby making it easier to extract features by image processing or visual inspection. However, smaller intervals also generally demand more computational resources.

With reference to U.S. Pat. No. 6,287,773 to Newell, a method for detecting known blocks of functionally aligned protein sequences in a test nucleic acid sequence, e.g., in an uncharacterized EST, is disclosed. The Newell '773 method involves: (a) reverse translating the set of protein sequences to a set of functionally aligned nucleic acid sequences using codon-usage tables and creating a profile from the set of functionally aligned nucleic acid sequences; (b) constructing a first indicator function (adenine) for the profile; (c) constructing a second indicator function (adenine) for the test nucleic acid sequence; (d) computing the Fourier transform of each of the indicator functions; (e) complex conjugating the Fourier transform of the second indicator function; (f) multiplying the Fourier transform of the first indicator function and the complex conjugated Fourier transform of the second indicator function to obtain a Fourier transform of the number of matches of adenine bases; (g) repeating steps (b)-(f) for guanine, thymine, and cytosine; (h) summing the Fourier transforms of the number of matches for each base, respectively, to obtain the total Fourier transform; (i) computing the inverse Fourier transform of the total Fourier transform to obtain a complex series; and (j) taking the real part of the series to determine the total number of base matches for the variety of possible lags of the profile relative to the test sequence. The first indicator function allows the value at a given position to be continuous between 0 and 1 as a function of the percentage presence of adenine at a particular position. The method can then detect the presence of known blocks of functionally aligned protein sequences in a test nucleic acid sequence based on the total number of base matches for the variety of possible lags, i.e., to facilitate sequence matching.

Despite efforts to date, a need remains for systems and methods that facilitate expeditious visualization of genomic information. In addition, a need remains for systems and methods that facilitate identification of repetitive DNA patterns, e.g., CpG islands, Alu repeats, non-coding RNAs, tandem repeats and various types of satellite repeats. A need remains for tools that can identify structurally or compositionally similar patterns that exhibit similar spectral properties. Such tools are to be contrasted with sequence alignment tools that seek to align sequences in linear order or nucleotide appearance. Still further, a need remains for systems and methods for facilitating rapid, full-scale analysis of spectral images using supervised and/or unsupervised machine learning techniques. Moreover, a need remains for systems and methods for increasing the resolution of spectral image sequences, e.g., to permit rapid visualization of an entire genome at a desired resolution. These and other needs are met by the systems and methods disclosed herein.

SUMMARY OF THE DISCLOSURE

The present disclosure provides advantageous systems and methods for facilitating DNA spectral analysis and, more particularly, systems and methods that employ image processing techniques and/or signal processing methods to automate and/or expedite, in whole or in part, the processing of DNA sequence data. As described in greater detail herein, exemplary systems and methods of the present disclosure support one or more of the following DNA spectral analysis techniques: (i) comparative histogram methodologies; (ii) selection/classification using support vector machines and genetic algorithms; (iii) unsupervised classification and discovery of structurally novel DNA segments; and (iv) spectro-video methodologies based on spectrogram extractions from DNA sequence data. The disclosed systems and methods offer numerous advantages, including (i) facilitating visualization of genomic information, (ii) identifying repetitive DNA patterns, e.g., CpG islands, Alu repeats, tandem repeats, satellite repeats, etc., (iii) rapid, full-scale analysis of spectral images using supervised and/or unsupervised machine learning techniques, and (iv) increasing the resolution of spectral image sequences, e.g., to permit rapid visualization of an entire genome at a varying and desired resolution.

According to a first aspect of the present disclosure, a DNA spectrogram is generated by applying Fourier transform to convert a symbolic DNA sequence consisting of letters A, T, C, G into a visual representation that highlights periodicities of co-occurrence of DNA patterns. The disclosed systems and methods facilitate the identification and/or location of repetitive DNA patterns by applying image processing operators to find prominent features in the vertical and horizontal direction of the DNA spectrograms. Rapid, full scale analysis of the derived spectral images is undertaken using supervised and unsupervised machine learning methods. In the supervised mode two exemplary methods to detect and classify repetitive DNA patterns according to the present disclosure include (a) a comparative histogram methodology, and (b) a technique that involves feature selection and classification using support vector machines and genetic algorithms.

The disclosed image processing operators are effective for identifying and/or locating DNA patterns, such as CpG islands, Alu repeats, non-coding RNAs (e.g., microRNAs and small nucleolar RNAs), tandem repeats, various type of satellite repeats, and the like. The image processing operators may be employed to identify and/or locate repetitive elements in a variety of biologic systems, e.g., within a chromosome, within a genome, or across genomes of various species. The disclosed system and method overcomes the limitations of existing methodologies, wherein a DNA sequence or genome is processed to generate huge numbers of spectrogram images, but such images fail to yield or elucidate the location of repetitive patterns and/or to associate a biological or clinical meaning to such repetitive patterns, in an efficient and reliable manner.

According to a second aspect of the present disclosure, a DNA spectrogram is generated by converting a DNA sequence to a binary indicator sequence and then applying short term Fourier transform and mapping to a color space in order to visualize the output. The DNA spectrogram is slid along DNA sequences to produce a video image. The video image—termed a "spectrovideo"—may be generated from very long DNA sequences to facilitate visualization thereof, e.g., long DNA sequences such as chromosomes or entire genomes. In contrast to a conventional DNA spectrogram of the same sequence, the disclosed spectrovideo provides enhanced resolution. In addition, the disclosed spectrovideo facilitates visualization of the genome in a short amount of time and at a desired resolution. Spectrovideo analysis may be employed to provide or facilitate a full genome analysis and/or to detect changes in full length DNA patterns (or desired portions thereof).

Scene change detection methods may be employed with respect to a spectrovideo to find breaks in linear visual features. Moreover, for each scene in a spectrovideo, statistical features may be extracted from the spectral domain. Furthermore, individual scenes from a full (or substantially complete) spectrovideo may be clustered using unsupervised clustering methods. Indeed, unsupervised video feature detection methods according to the present disclosure may be employed to identify and/or reveal genome-wide similarities at the spectral DNA level. Such analytic techniques can thus be employed for automatic DNA analysis, e.g., to find gene networks, important motifs, repetitive DNA elements, and other prominent DNA patterns.

Additional advantageous features and functions of the disclosed systems and methods will be apparent from the detailed description which follows, particularly when read in conjunction with the appended figures.

BRIEF DESCRIPTION OF APPENDED FIGURES

To assist those of ordinary skill in the art in making and using the disclosed systems and methods, reference is made to the accompanying figures, wherein:

FIG. 1 sets forth exemplary binary indicator sequences (BISs) for a DNA sequence according to spectral imaging techniques employed according to the present disclosure;

FIG. 2 sets forth plots of the exemplary BISs set forth in FIG. 1 hereto;

FIG. 3 sets forth discrete Fourier transforms (DFTs) for the exemplary BISs of FIGS. 1 and 2;

Figure 6:
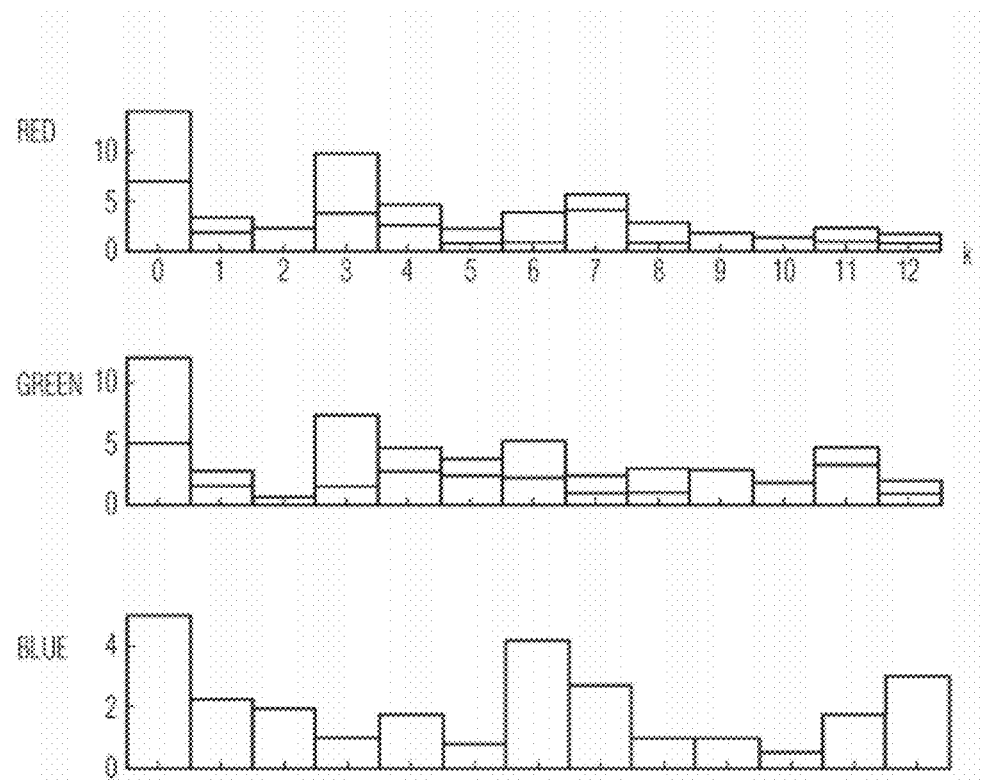
Figure 7:
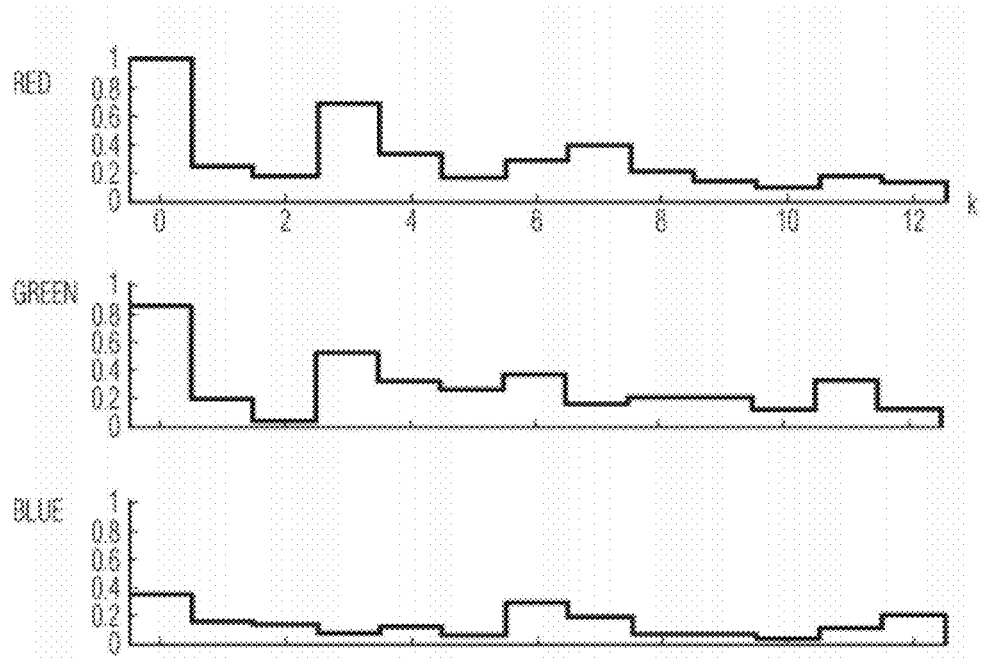
Figure 8:
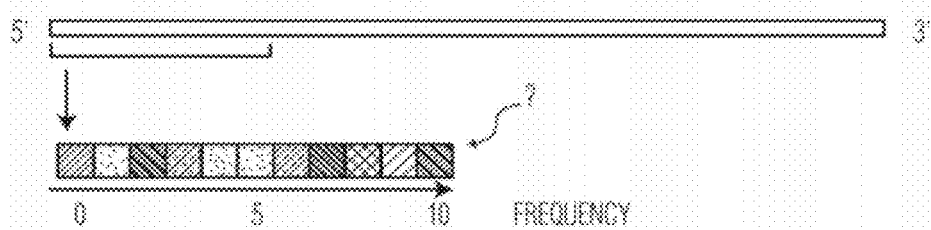
Figure 8:
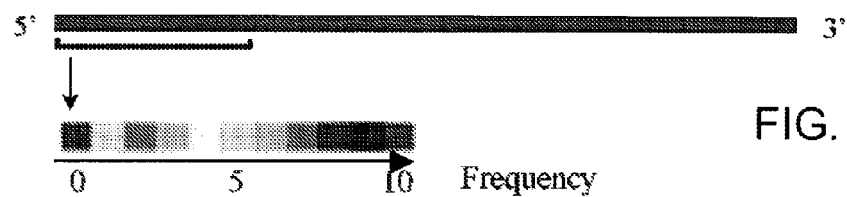
Figure 9:
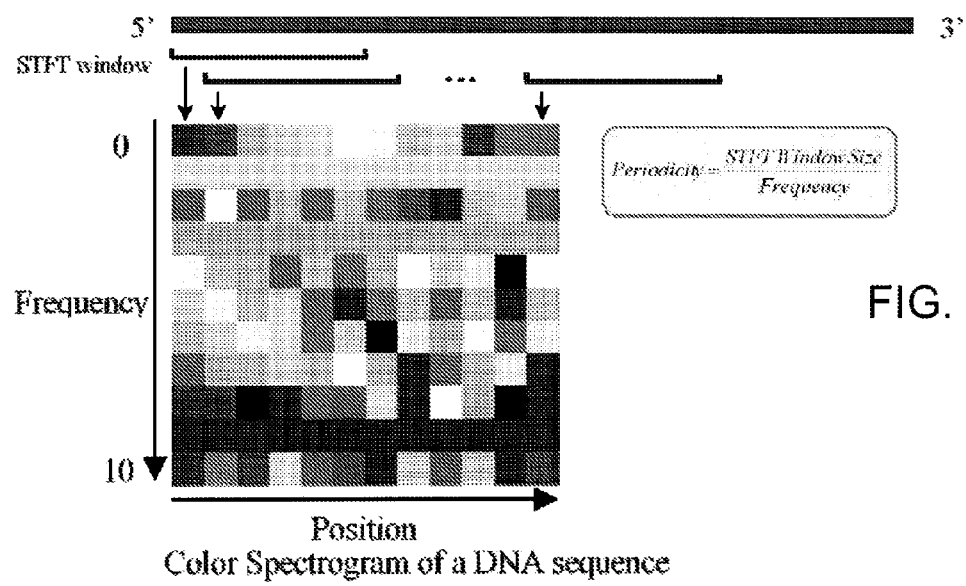
Figure 10:
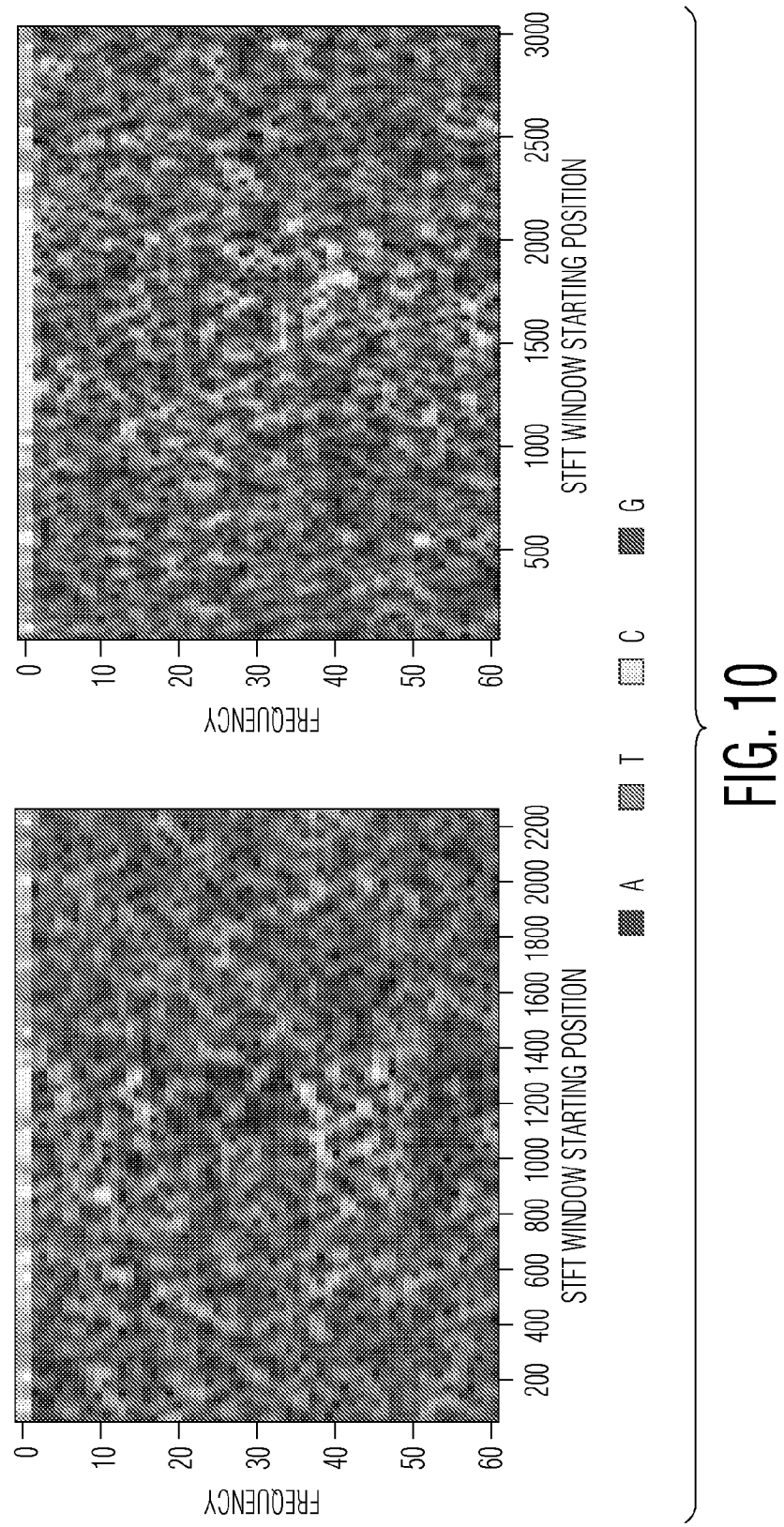
Figure 11:
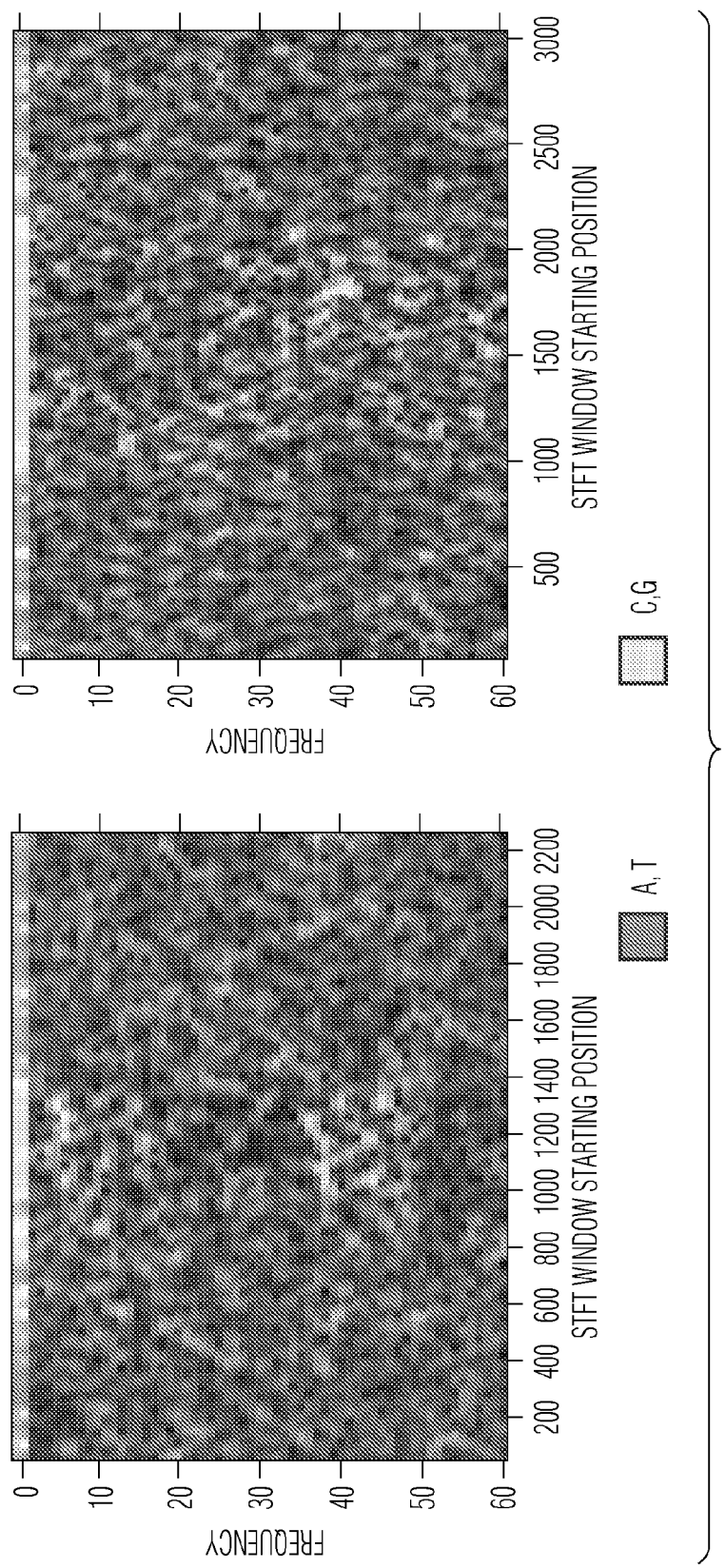
Figure 12:
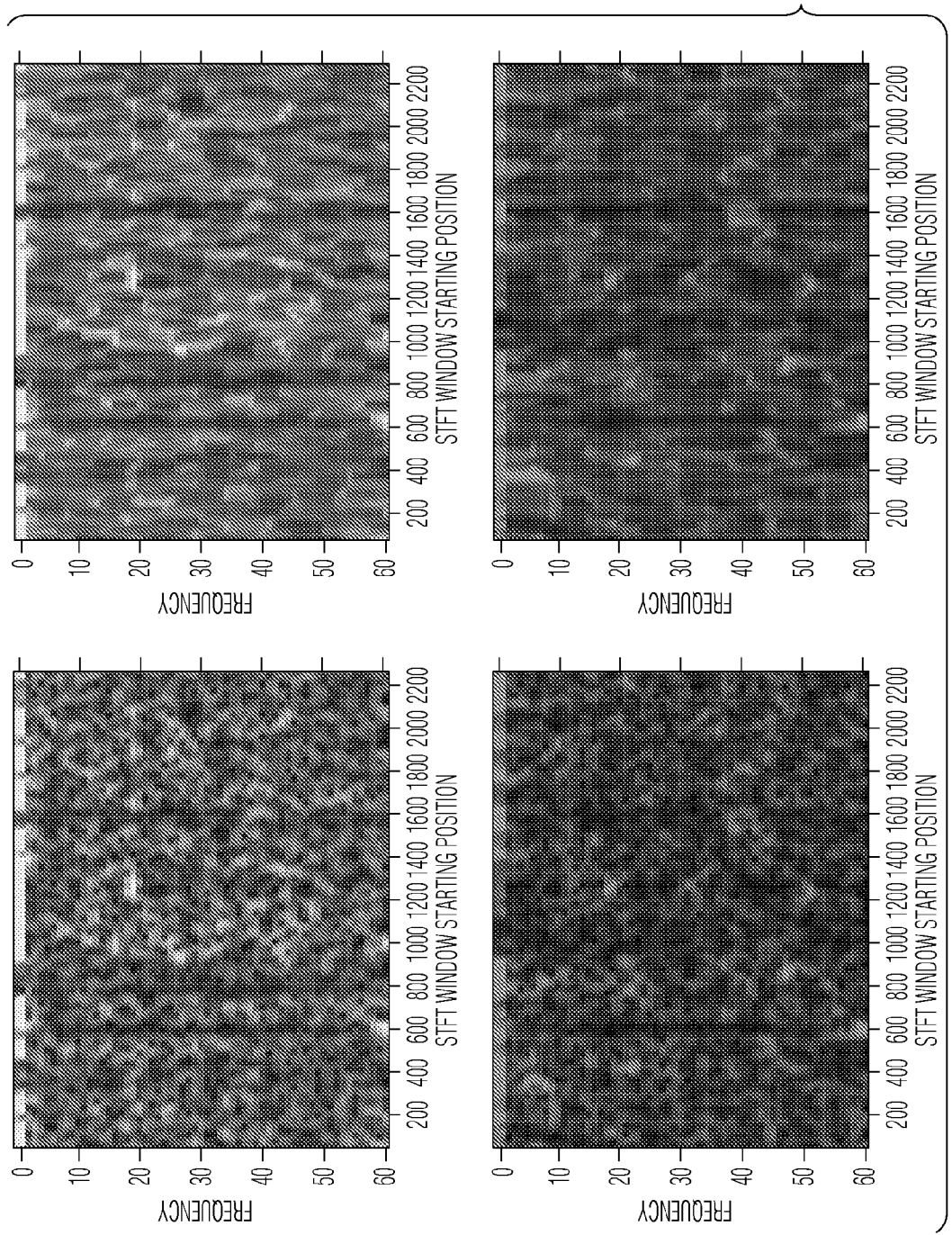
Figure 13:
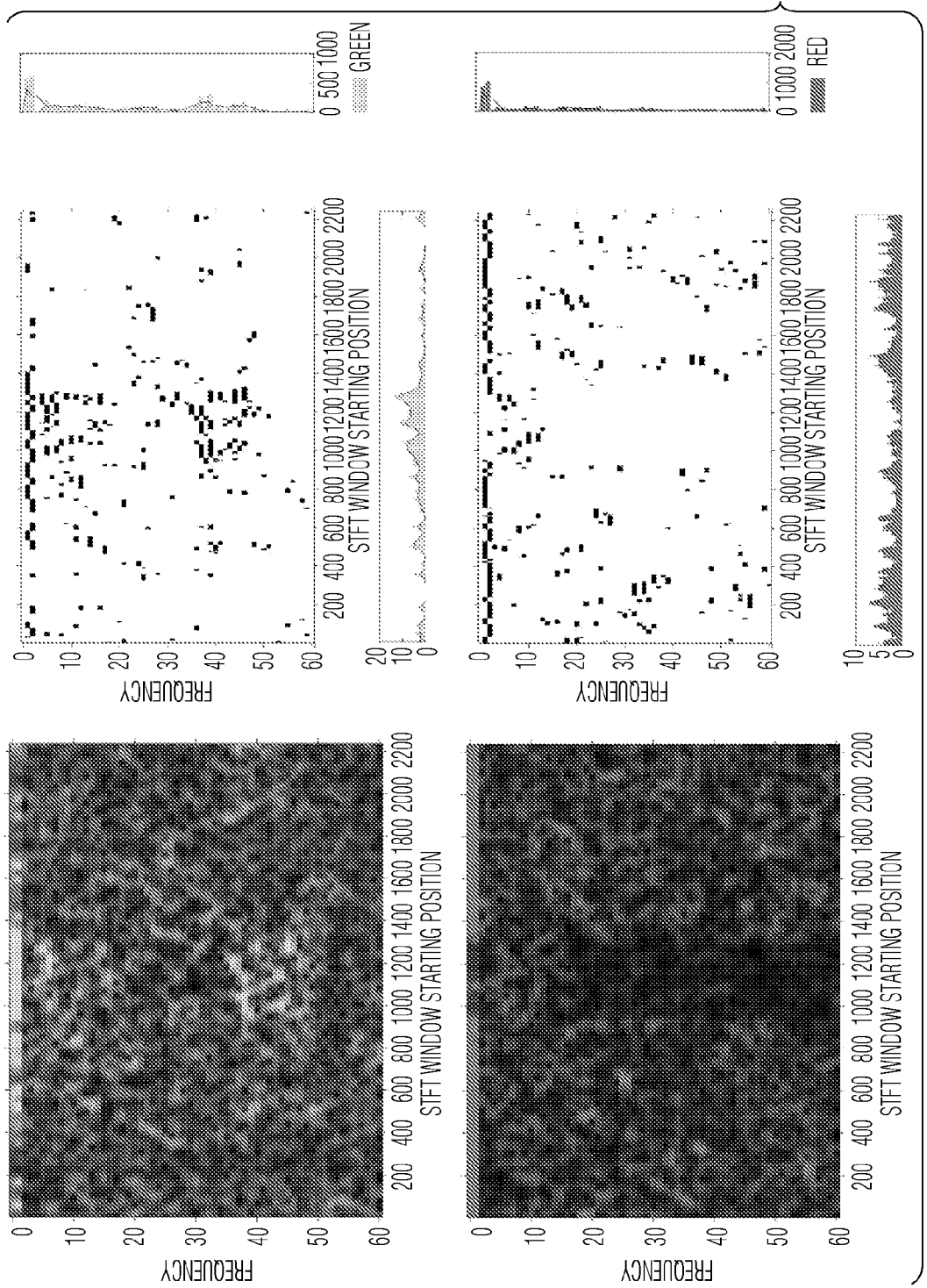
Figure 14:
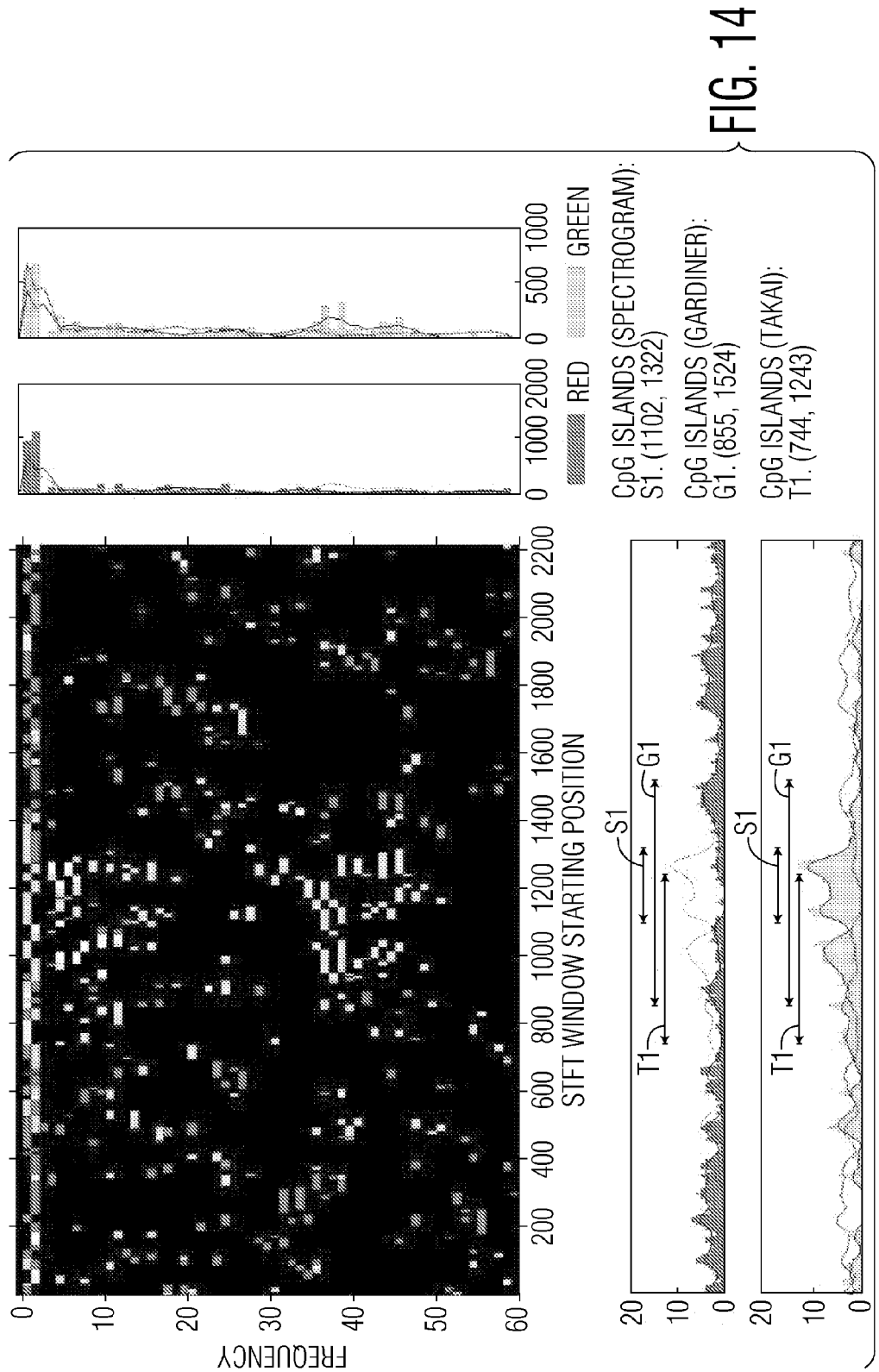
Figure 15:
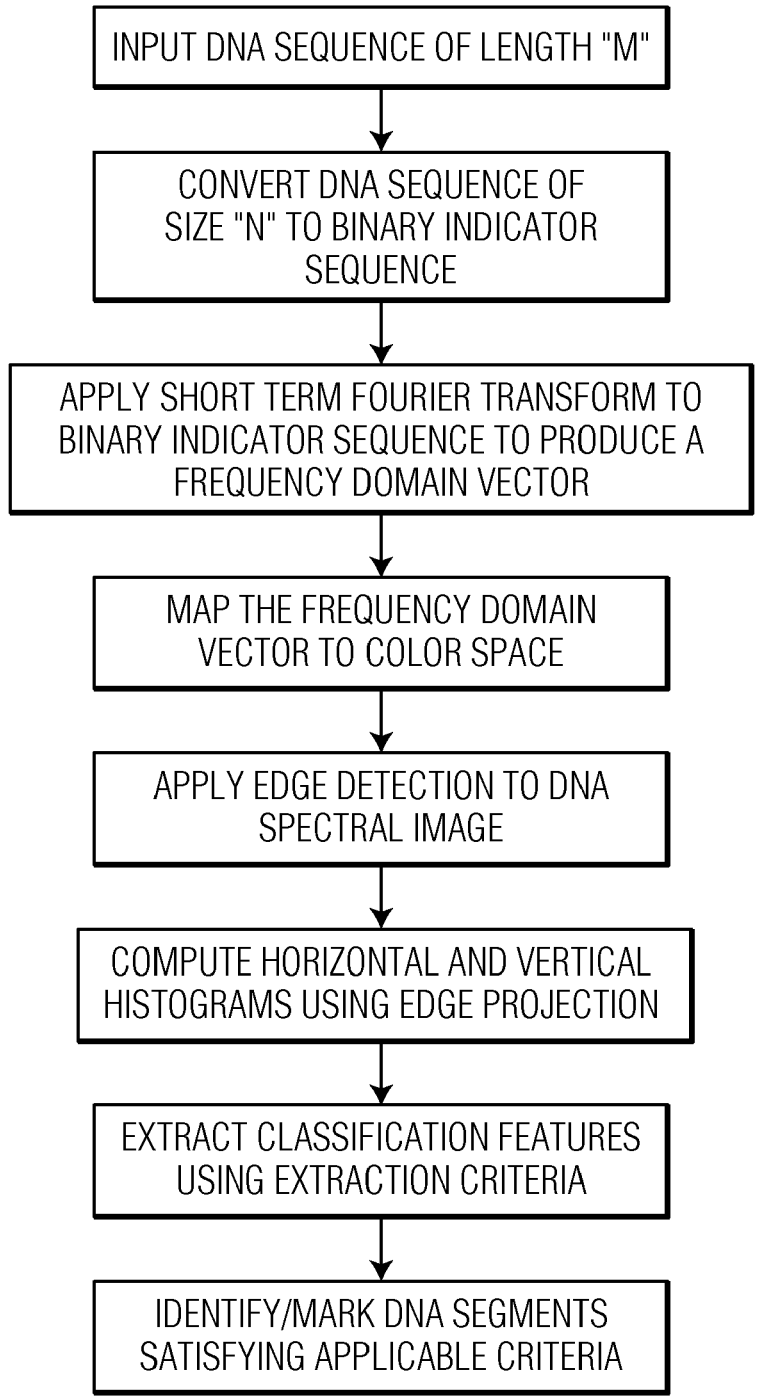
Figure 16:
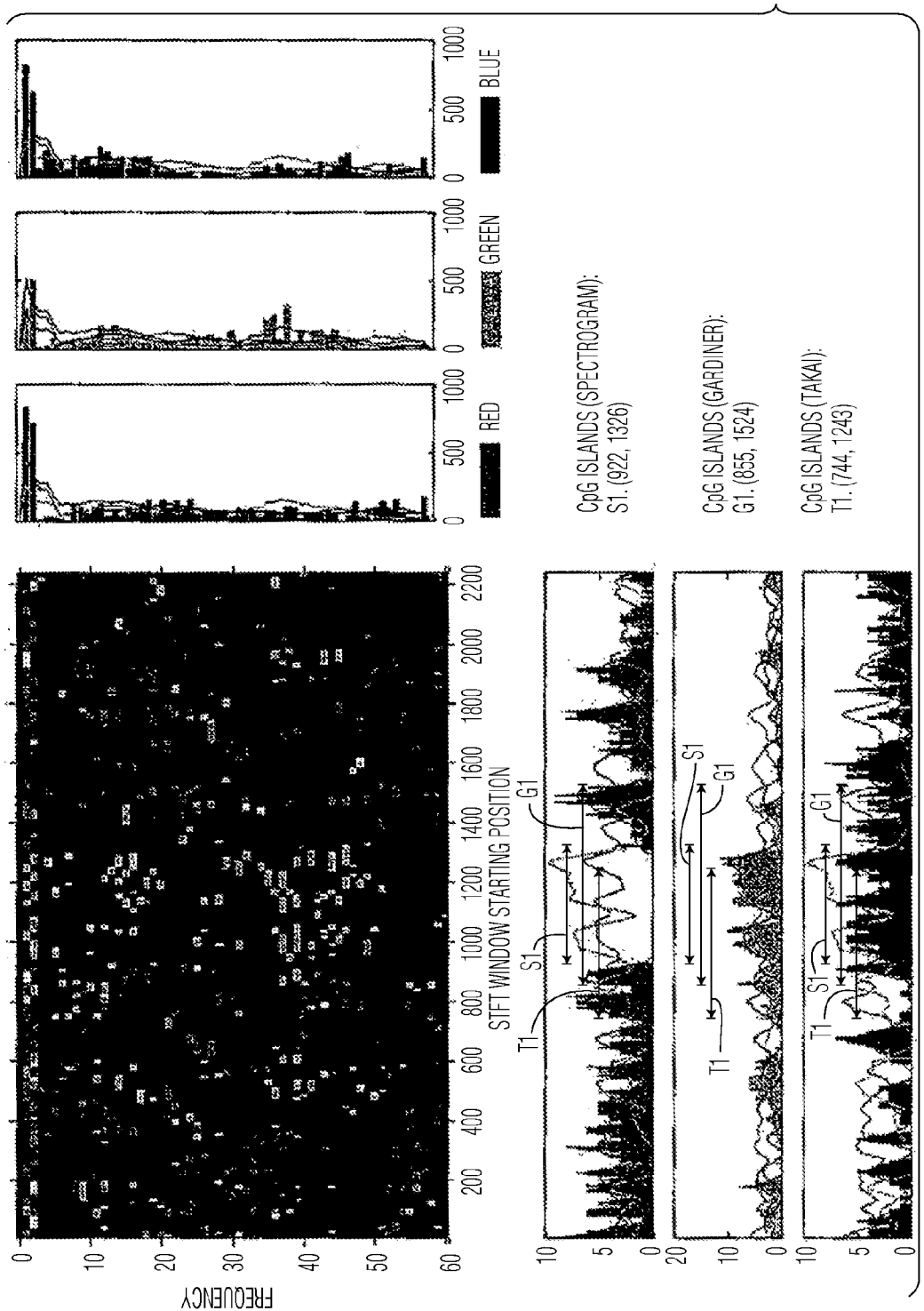
Figure 17:
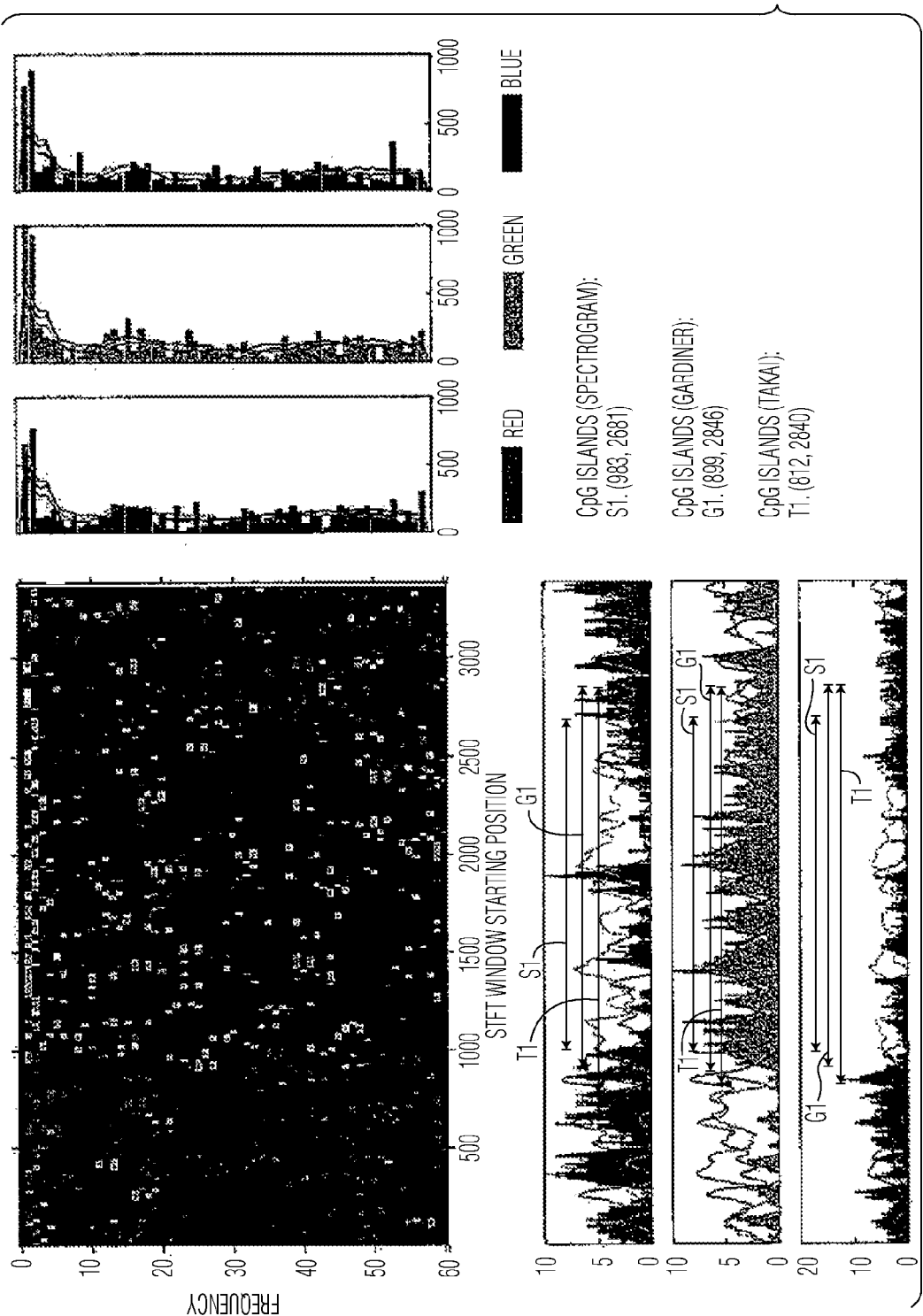
Figure 18:
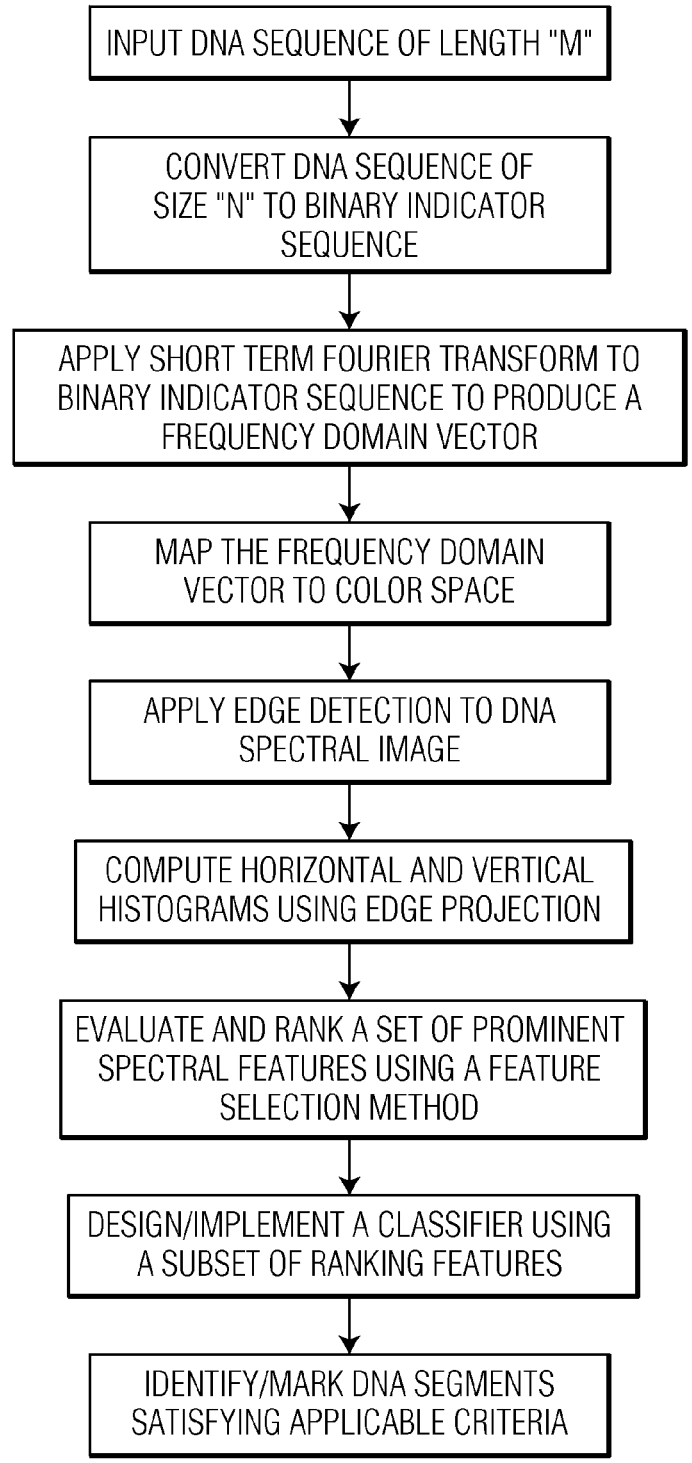
Figure 19:
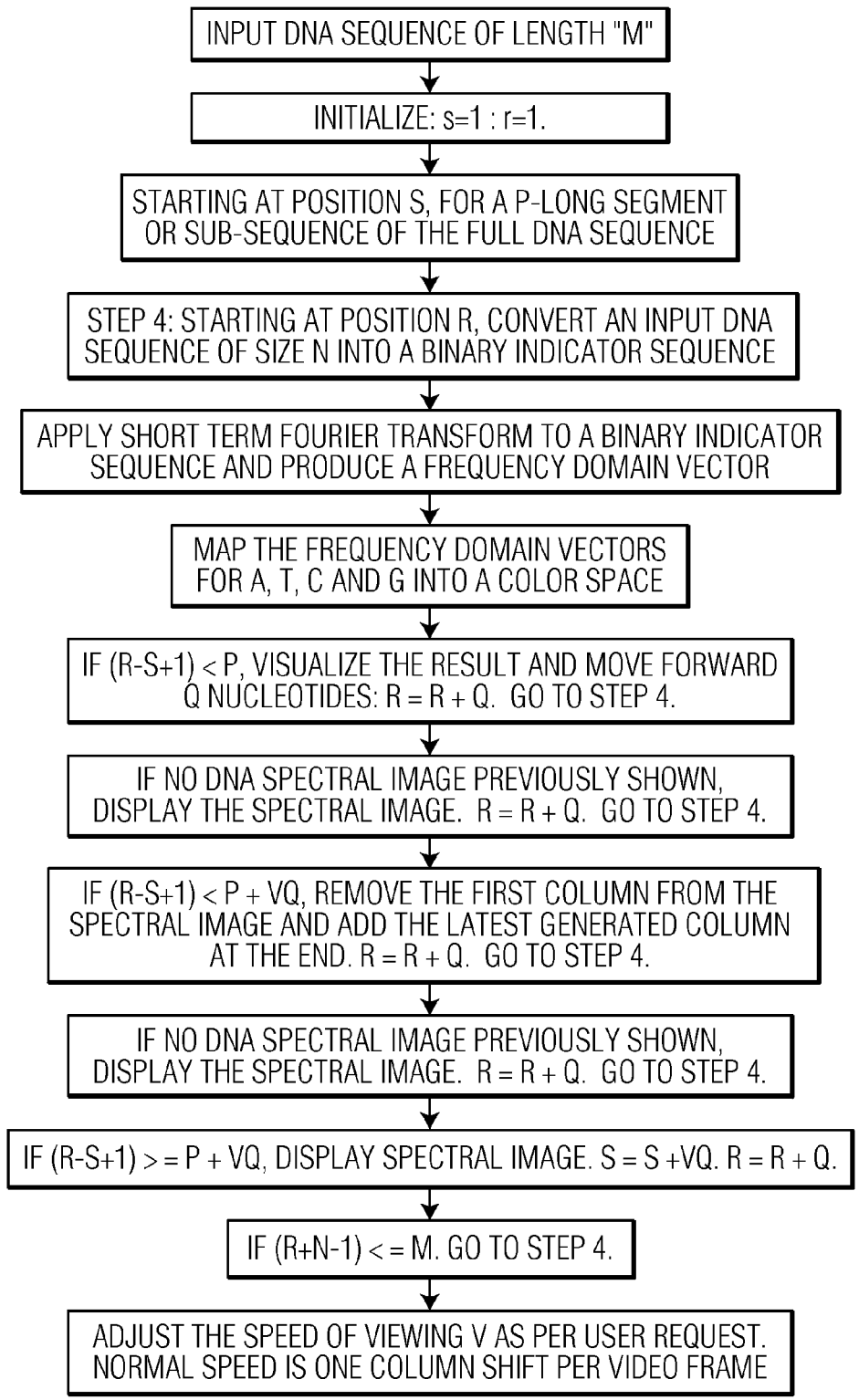
Figure 20:
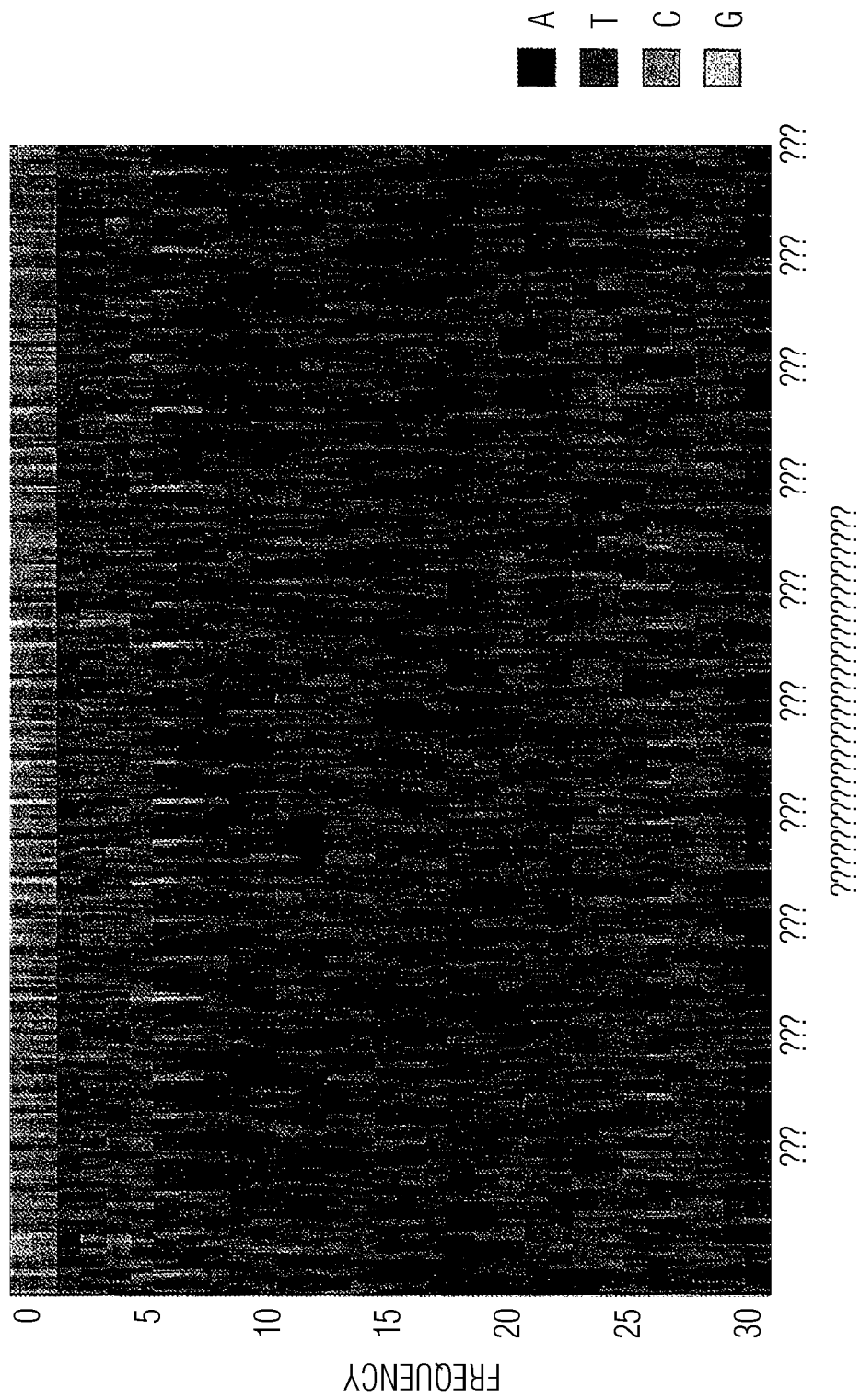

FIG. 6 sets forth the summation of DFT values in color space according to the present disclosure;

FIG. 7 sets forth normalized plots of the DFT summation values in color space;

FIG. 8 is an exemplary color spectrum for a DNA sequence (reproduced in gray scale);

FIG. 9 is an exemplary concatenation of a plurality of color spectra strips for exemplary DNA segments according to the present disclosure;

FIG. 10 are spectrogram images of exemplary CpG islands;

FIG. 11 are spectrogram image of the CpG islands of FIG. 10, limited to red and green colors;

FIG. 12 sets forth a series of denoised spectrograms according to the present disclosure;

FIG. 13 are spectral images and edge measurements for green- and red-based spectrograms according to the present disclosure;

FIG. 14 sets forth edges extracted from an exemplary RGB-based spectrogram and related CpG island classification associated therewith;

FIG. 15 sets forth a flowchart for an exemplary comparative histogram method/technique according to the present disclosure;

FIGS. 16 and 17 are exemplary plots showing CpG island detection using edge histograms on spectrograms derived using color mapping;

FIG. 18 sets forth a flowchart for an exemplary genetic algorithm-support vector machine (GA-SVM) method/technique according to the present disclosure;

FIG. 19 sets forth a flowchart for an exemplary method/technique for generating a spectrovideo according to the present disclosure; and FIG. 20 is an image from an exemplary spectrovideo according to the present disclosure.

DESCRIPTION OF EXEMPLARY EMBODIMENT(S)

The systems and methods of the present disclosure facilitate DNA spectral analysis. As described herein, exemplary systems and methods support and/or utilize one or more of the following DNA spectral analysis techniques: (i) comparative histogram methodologies; (ii) selection/classification using support vector machines and genetic algorithms; and (iii) spectrovideo methodologies based on spectrogram extractions from DNA sequence data. Many benefits may be realized according to the present disclosure, e.g., (i) enhanced visualization of genomic information, (ii) identification of repetitive DNA patterns, e.g., CpG islands, Alu repeats, non-coding RNAs, tandem repeats, satellite repeats, etc., (iii) unsupervised classification and discovery of structurally novel DNA segments; (iv) rapid, full-scale analysis of spectral images using supervised and/or unsupervised machine learning techniques, and (iv) increased resolution of spectral image sequences, e.g., to permit rapid visualization of an entire genome at a desired resolution.

According to the disclosed systems and methods, DNA spectrograms are generated in a conventional manner, as described in greater detail herein above with reference to FIGS. 1-9. For example, a conventional algorithm or technique for the generation of DNA spectrograms may be employed that entails the following five steps:

(i) Formation of Binary Indicator Sequences (BISs) $u_A[n]$, $U_T[n]$, $u_C[n]$ and $U_G[n]$ for the four nucleotide bases. As noted above, an exemplary BIS pattern is reproduced in FIG. 1 hereto and a plot of the BIS values is presented in FIG. 2.

(ii) Discrete Fourier Transform (DFT) on BISs. The frequency spectrum of each base is obtained by computing the DFT of its corresponding BIS using Equation (1) (reproduced below):

$$U_X[k] = \sum_{n=0}^{N-1} u_X[n] e^{-j\frac{2\pi}{N}kn}, k = 0, 1, \ldots, \lfloor N/2 \rfloor + 1 \quad (1)$$

$$X = A, T, C, \text{ or } G$$

Figure 3:
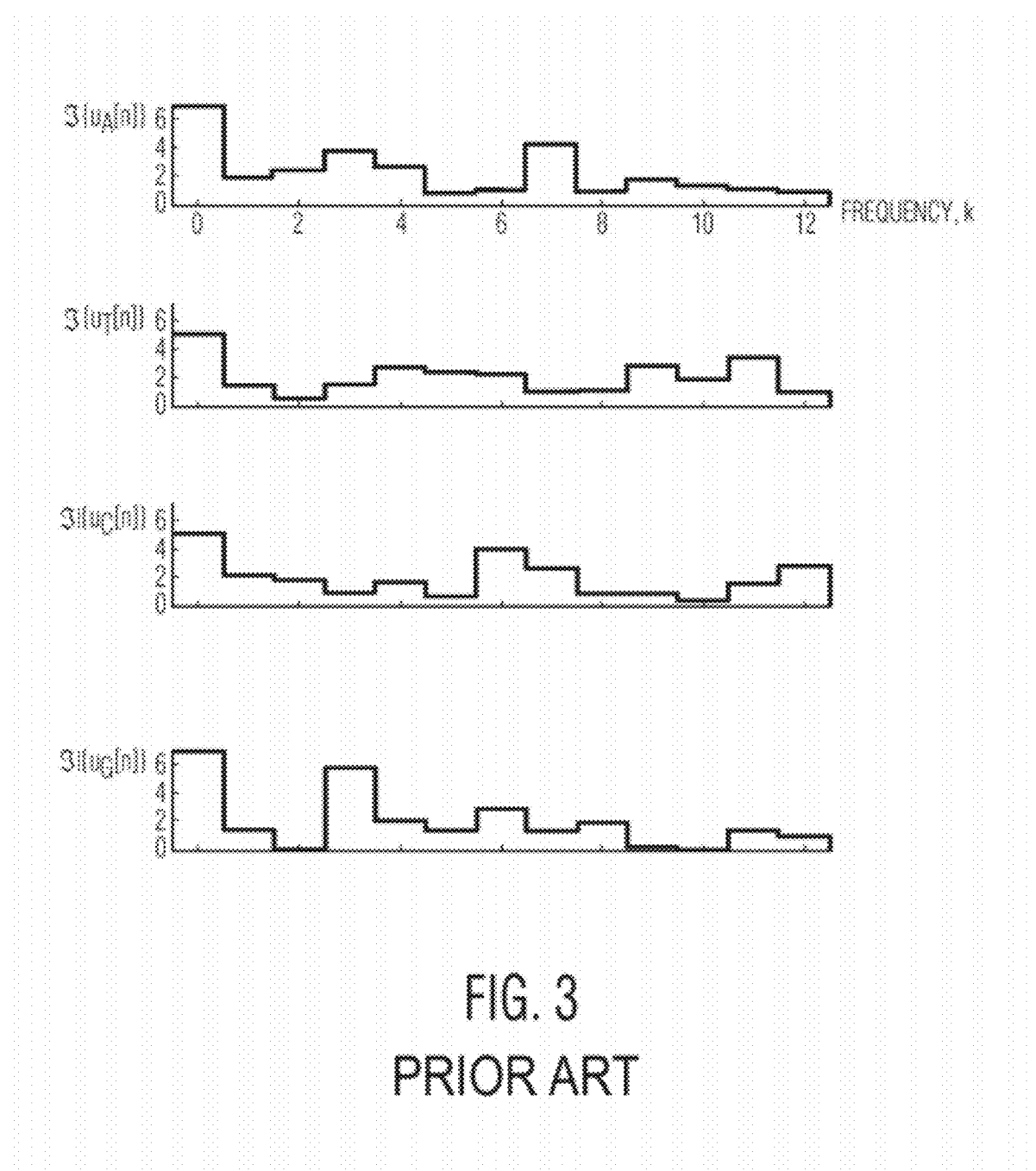
Figure 4:
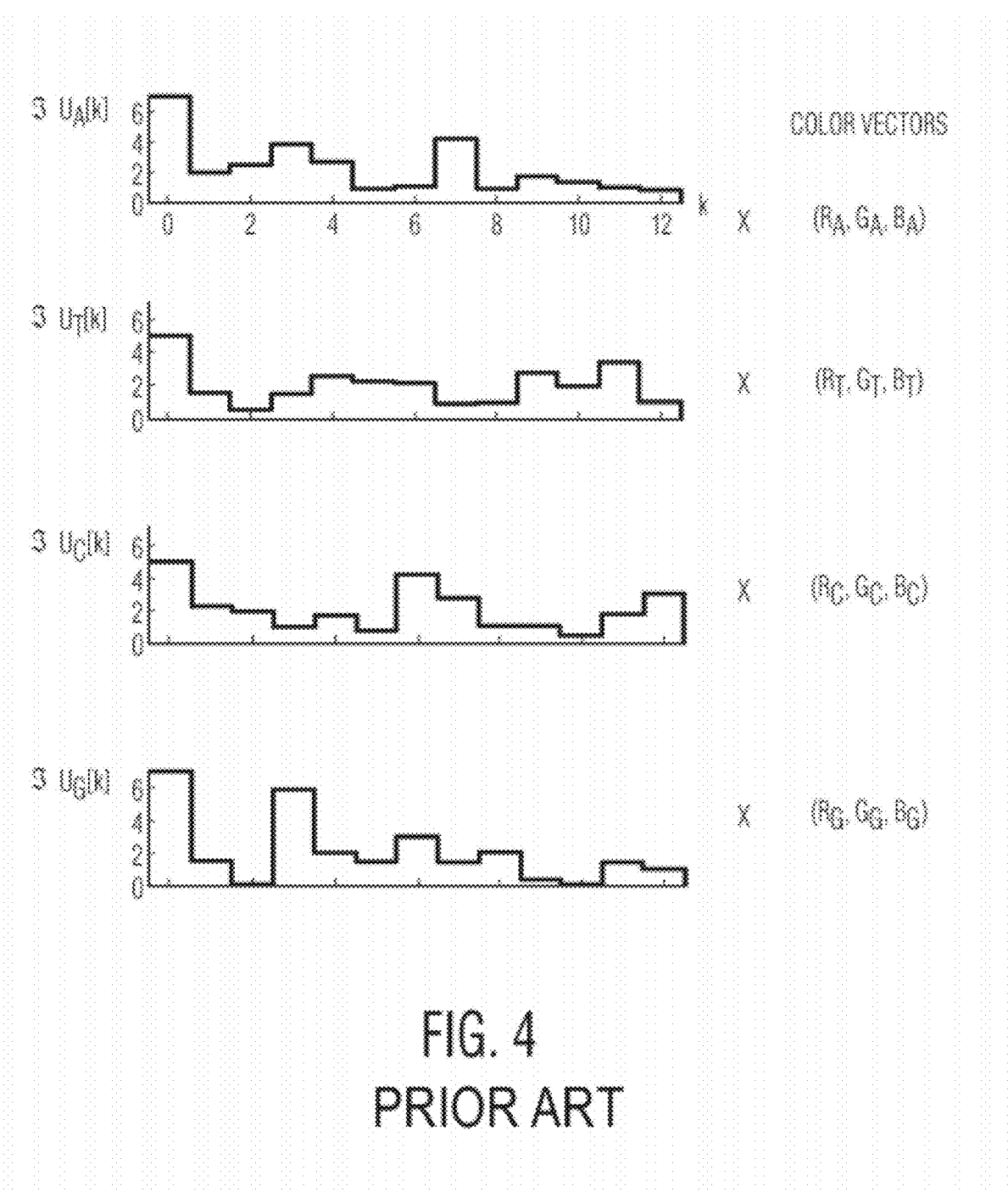
FIG. 4 illustrates the mapping of the exemplary DFT values of FIG. 3 to color space.

As illustrated in FIG. 3, the sequence U[k] provides a measure of the frequency content at frequency k, which is equivalent to an underlying period of N/k samples.

Figure 5:
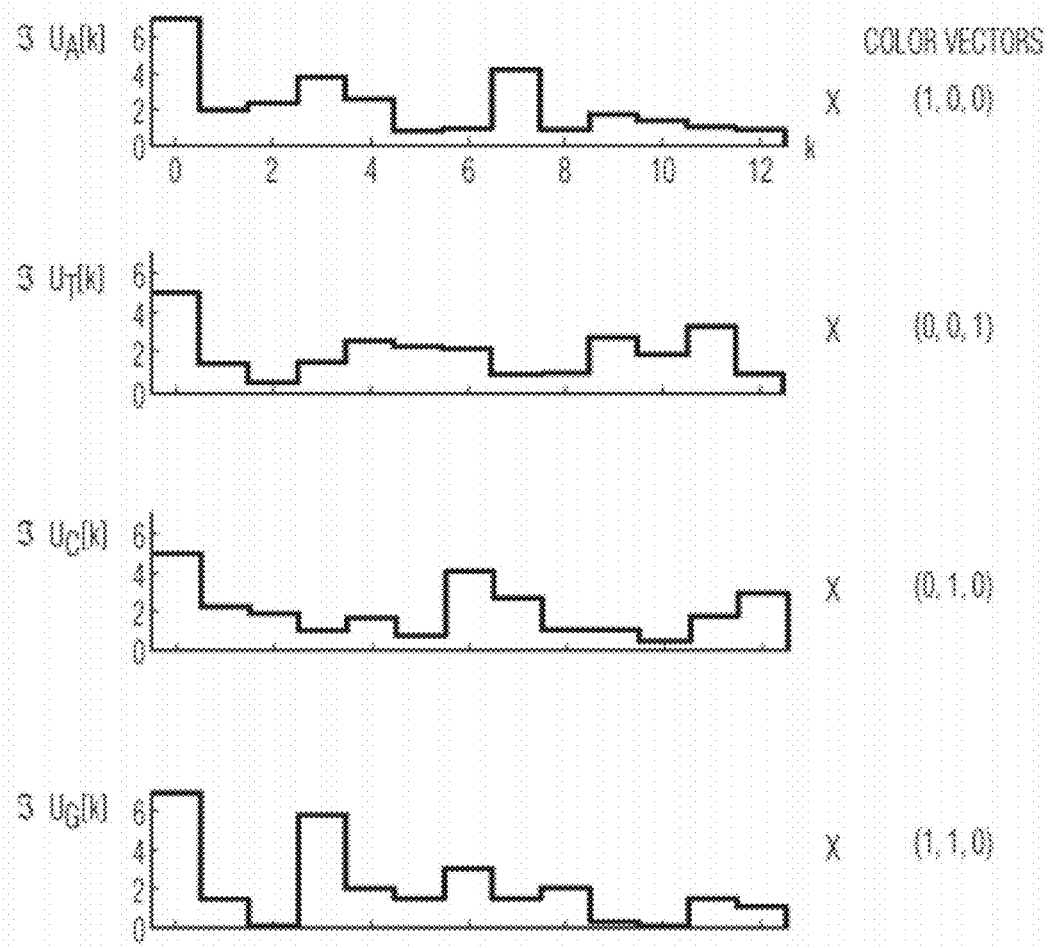
FIG. 5 illustrates the mapping of the exemplary DFT values of FIG. 3 to color space based upon illustrative color vectors.

(iii) Mapping of DTF Values to RGB Colors. The four DFT sequences are reduced to three sequences in the RGB space by a set of linear equations which are reproduced below:

$$X_r[k] = \alpha_r U_A[k] + t_r U_T[k] + c_r U_C[k] + g_r U_G[k]$$

$$X_g[k] = \alpha_g U_A[k] + t_g U_T[k] + c_g U_C[k] + g_g U_G[k]$$

$$X_b[k] = \alpha_b U_A[k] + t_b U_T[k] + c_b U_C[k] + g_b U_G[k] \quad (2)$$

where $(\alpha_r, \alpha_g, \alpha_b)$, $(t_r, t_g, t_b)$, $(c_r, c_g, c_b)$ and $(g_r, g_g, g_b)$ are the color mapping vectors for the nucleotide bases A, T, C and G, respectively. The resultant pixel color $((X_r[k], X_g[k], X_b[k])$ is thus a superposition of the color mapping vectors weighted by the magnitude of the frequency component of their respective nucleotide base (see FIG. 4). Mapping of DFT values to colors is illustrated in FIGS. 5 and 6

(iv) Normalizing the Pixel Values. Before rendering the color spectrograms, the RGB values of each pixel are generally normalized so as to fall between 0 and 1. FIG. 7 presents exemplary normalized plots of the combined DFT values of FIG. 6.

(v) Short-Time Fourier Transform (STFT). A DNA spectrogram is formed by a concatenation of individual DNA sequence strips, where each strip generally depicts the frequency spectrum of a local DNA segment (see FIGS. 8 and 9).

According to the present disclosure, CpG islands may be advantageously extracted from the DNA spectral images generated hereby. CpG islands are important biological markers for the promoter regions of genes in organisms containing 5-methylcytosine in their genomes, and CpG islands play important roles in cell differentiation and in the regulation of gene expression in vertebrates. CpG islands have been defined by Gardiner-Garden and Frommer as regions with at least 200 base pairs (bp), a C+G content greater than 50% and an observed/expected CpG ratio larger than 0.6. CpG islands have also been defined by Takai and Jones as regions longer than 500 bp, with a C+G nucleotide content of at least 55% and an observed/expected CpG ratio of 0.65. It is noted that the Takai and Jones definition is targeted at returning CpG islands more likely to be associated with the 5' regions of genes and at excluding most Alu-repetitive elements. In both definitions, the observed/expected CpG ratio is given by (number of C×number of G/length of the segment).

With reference to FIG. 10, two exemplary spectrograms are providing showing a CpG island at the center. The size of the STFT window is chosen to be 120 base pairs (bp), with an overlap of 119 bp between adjacent windows. It is noted that in the extraction of a CpG from a spectral image, it is generally not necessary to differentiate A from T, and C from G.

Therefore, instead of using four color vectors respectively for the four nucleotide bases, two color vectors may be used, e.g., red (1, 0, 0) for A and T and green (0, 1, 0) for C and G. The corresponding spectrograms are shown in FIG. 11 and, in both images, the CpG islands contrast the background better. This choice of color vectors also permits consideration of only the red and green color components, while the blue component may be ignored. Thus, the disclosed color selection technique permits and/or facilitates generation of images wherein features are more distinguishable, i.e., enhanced extraction performance is achieved by adopting optimal color scheme(s).

Generally, image feature detection methods may involve three steps: (i) image denoising, (ii) extraction of classification features, and (iii) decision-making by evaluating the classification features. For purposes of the disclosed systems and methods, denoising of the spectral images is not required, although enhanced results may generally be achieved by including an appropriate denoising step.

Image Denoising

A raw spectrogram image contains noise, the removal of which can improve or enhance detection reliability, efficiency and/or performance. Denoising of a spectrogram image can be achieved using one or more morphological operations. For example, by performing morphological opening followed by morphological closing, small regions of weak pixels can be removed. Thereafter, regions containing strong pixels that are close together can be merged. Denoising is generally undertaken separately in the green and red color spaces. The shape and size of the structural elements for the morphological operations are carefully chosen so that noise is filtered out, while useful details are retained in the spectrogram. Rectangular structuring elements with a height of one and a length of fifty pixels have been found to provide effective parameters for denoising operations in connection with the detection of CpG islands. Exemplary denoised spectrograms are presented in FIG. 12 hereto, wherein the left-hand images include the green and red channel images only, and the corresponding right-hand images after morphological "close" followed by "open" filter.

Extraction of Classification Features

It has been noted through visual inspection that in CpG islands, the intensity of the green color is generally stronger (presence of C and G) than the red (presence of A and T). In addition, the intensity of the red color is typically evenly low—i.e., substantially uniform—in the region, whereas there is a larger fluctuation in intensity in the green space, which is evident from one or more clusters of bright spots. To address the foregoing issues of uniformity/non-uniformity, systems and methods of the present disclosure advantageously facilitate enhanced extraction of classification features. Thus, according to exemplary embodiments of the present disclosure, 'Sobel' edge detection is performed on the denoised spectrogram in the green and red spaces respectively. As is generally known in the art, the Sobel operator is a discrete differentiation operator that computes an approximation of the gradient of the image intensity function. At each point in the image, the result of the Sobel operator is either the corresponding gradient vector or the norm of this vector. Alternative edge detection techniques may be employed, e.g., Canny edge detector, without departing from the spirit or scope of the present disclosure.

Application of Sobel edge detection to a denoised spectrogram yields binary images of edges, which correspond to pixels having larger intensity differences from their neighbors. It has generally been found that there are more edge pixels for CpG islands in the green space than in the red space.

The binary images generated through edge detection are further processed by counting the number of edge pixels along the x-axis (STFT window position) and the y-axis (spectral frequency), respectively. Four histograms are obtained as a result: x- and y-histograms for the green and red spaces. Finally, the foregoing histograms are smoothed by computing moving averages for each.

Exemplary spectral images reflecting edge readings for green- and red-based spectrograms are set forth in FIG. 13. The left column of FIG. 13 shows the original image, while the right column shows the corresponding image after applying Sobel edge detection with a square 2×2 mask. The images on the right show horizontal and vertical edge histograms.

Thus, the extraction of classification features is influenced by a series of parameters that may be addressed according to the systems and methods of the present disclosure. Among the parameters that affect the extraction of classification features and that are controlled according to the present disclosure are: (i) the method of edge detection, (ii) the threshold for edge detection, and (iii) the size of the moving-average window.

Decision-Making Through Evaluation of Classification Features

Once the classification features of a spectral image have been identified, it is contemplated according to disclosed systems/methods that a classifier for CpG islands may be provided. Two exemplary approaches for generating a classifier are (i) a fixed-threshold approach, and (ii) a genetic algorithm/support vector machine (GA-SVM) approach.

In the disclosed fixed-threshold approach, CpG islands are advantageously extracted in the following way:
(i) (x_histogram_green−x_histogram_red)>threshold (=2 in this example)
(ii) Regions satisfying (1) of length<200 bp are rejected.
(iii) Regions satisfying both (1) & (2) separated by less than 100 bp are merged.

With reference to FIG. 14, the edges are extracted from a color spectrogram which maps the bases 'A', 'T' to the red color, and 'C', 'G' to the green color. The edge pixels, which may displayed in red and green, are extracted from the corresponding color spaces independently. A further color, e.g., a yellow color, may be used to display results associated with coexistence of both red and green edges. As is apparent from exemplary FIG. 13, the count of the green pixels in the histograms along the x-axis clearly exceeds that of the red pixels for the CpG island. Based on CpG island identification criteria set froth above, a CpG island is identified as being located from 1102 to 1322 nucleotides of the DNA segment. For comparison purposes, the CpG islands based on Gardiner's and Takai's CpG definitions are also shown in FIG. 14, i.e., Gardiner (855, 1524) and Takai (744, 1243). Of note, the CpG island identification criteria set forth herein is more stringent as compared to Gardiner's and Takai's definition/criteria, at least for purposes of the exemplary spectrogram presented in FIG. 14. As will be readily apparent to persons skilled in the art, the CpG island identification criteria is adjustable through variation of the applicable parameter values.

Thus, in a broader sense, an exemplary histogram comparative system and method according to the present disclosure involves the following steps, a flowchart for which is presented in FIG. 15. Although the order in which the steps are presented herein is representative of the disclosed system/method, it is to be understood that the disclosed system and method are not limited to the order presented herein. Moreover, the disclosed system and method do not exclude the introduction of one or more additional steps that may further enhance or facilitate the identification process, nor are the disclosed system and method limited in scope to implementations entail each and every step disclosed herein, as is readily apparent from the detailed description provided herein.

Exemplary Comparative Histogram/Fixed Threshold Processing System and Method

1. Input a DNA sequence of length M to the disclosed system/method:
   Parameters:
      N—STFT window size,
      q—overlap,
      p—viewing resolution (where M>>p>N)
2. Convert the input DNA sequence of size N into a binary indicator sequence;
3. Apply short term Fourier transform (STFM) to the binary indicator sequence and produce a frequency domain vector;
4. Map the frequency domain vectors for A, T, C and G into a color space, e.g., RGB (red-green-blue) or HSV (hue-saturation-value) color space;
5. Apply edge detection to the DNA spectral image using a conventional edge detection method (e.g., a Sobel or Canny edge detector);
6. Compute horizontal and vertical histograms for red, green, blue components from RGB (or HSV components if HSV color space is used) separately by using edge projection. The histograms can also represent combined colors. For example, C and G can be combined and represented by a green component and A and T can be combined to represent a red component;
7. Evaluate histogram data. For example, for CpG islands, the following extraction criteria may be employed:
   (1) (x_histogram_green−x_histogram_red)>threshold (e.g., equal to 2)
   (2) Regions satisfying (1) of length<200 bp are rejected.
   (3) Regions satisfying both (1) & (2) separated by less than 100 bp are merged.
8. DNA segments that satisfy the evaluation criteria are marked as repetitive element(s) and the start and end position are noted/recorded (e.g., CpG island). There are other types of DNA sequences that may exhibit repetitive characteristics at the structural level for whole genomes and/or across genomes. Recently, it has been recognized that important functional roles may be performed by and/or associated with non-coding RNAs. The DNA sequences that give rise to hairpin structures represent a class of such non-coding RNAs. For example, MicroRNAs (miRNAs) are small RNAs that regulate gene expression post-transcriptionally. David Bartel, a biology professor at the Whitehead Institute at the Massachusetts Institute of Technology, predicts that miRNAs could regulate one third of all human genes (*Cell*, Cell Press, Jan. 14, 2005).

The disclosed processing techniques are typically implemented through appropriate software/programming that is run/operated on an appropriate processing unit. The processing system may be free-standing, e.g., a personal computer, or associated with a network (intranet, extranet, distributed network that communicates across the Internet, etc.). The processing unit/system typically communicates with appropriate memory/storage, e.g., for purposes of accessing software/programming, databases that contain parameters and values associated with the disclosed systems/methods, and for storage (both short-term and long-term) of values/data/images generated through the disclosed systems/methods. The disclosed processing unit/system also typically communicates with one or more output systems for displaying and/or recording the values/data/images generated according to the present disclosure, e.g., printer(s), monitor(s), and the like. Thus, in short, the disclosed systems and methods are susceptible to computer and/or processor-based implementations, as are known to persons skilled in the art.

Turning to exemplary GA-SVM approaches/techniques according to the present disclosure, a support vector machine with genetic algorithm is utilized to evaluate and rank the quality of a set of features, e.g., a set of image-based features. In exemplary embodiments, the disclosed evaluation/ranking functionality are effective to identify, for example, CpG islands. In addition, recursive feature elimination method(s) and/or principal component analysis may be employed to find prominent features. Of note, existing CpG island definitions, like those by Gardiner and Takai, guide implementation of the disclosed systems and methods, although alternative definitions may be accommodated, as will be readily apparent to persons skilled in the art. A typical goal of the disclosed GA-SVM approach/technique is to find features that are useful for CpG island classification.

The disclosed GA-SVM approach/technique generally involves use of a support vector machine with genetic algorithm to evaluate and rank the quality of a set of features, e.g., for identifying CpG islands. Thus, for example, the disclosed GA-SVM approach/technique may be employed to extract a predetermined number of features, e.g., 127 features, from each DNA segment having a given length, e.g., a DNA segment that is 200 bases in length. According to exemplary embodiments of the present disclosure, the composition of the feature set is as follows (total features=127):

Number of green pixels (1)
Number of red pixels (1)
Number of green edge pixels (1)
Number of red edge pixels (1)
Number of green edge pixels minus number of red edge pixels (1)
Red edge histogram count along the frequency axis (61)
Green edge histogram count along the frequency axis (61)

Various CpG island definitions may be employed, e.g., Gardiner's and/or Takai's CpG island definition. Based on the selected definition, a large number of features is typically generated according to the disclosed GA-SVM approach/technique, e.g., 127 features for each spectrogram image. In total, according to an exemplary embodiment of the present disclosure, 3206 DNA segments were used, such segments being converted to spectrograms. The features sets are extracted from spectrograms representing CpG or non-CpG classes.

According to the present disclosure, a predetermined percentage of the input data is used to "train" the support vector machine, e.g., two-thirds of the input data may be used for training the SVM (see table below). The remaining data (e.g., one third of the total) are used for testing purposes according to the disclosed GA-SVM approach/technique. Preliminary results have shown that out of the 127 features noted above, the best feature set consists of 57 elements, and an optimum accuracy of 67% has been achieved.

An exemplary GA-SVM approach/technique according to the present disclosure involved the following operational parameters:

Total Number of Sequences:

| Use of Feature Sets | CpG Islands | Non-CpG Islands | Total |
|---|---|---|---|
| Training | 1422 | 678 | 2100 |
| Testing | 746 | 360 | 1106 |
| Overall | 2168 | 1038 | 3206 |

Number of Trials: 100,000

As described herein, the exemplary implementations are based on a color-mapping scheme that groups the bases 'A', 'T' and 'C', 'G' into the red and green colors, respectively. In such implementations, it is only necessary to consider the red and green color components in the extraction algorithms for identification of CpG islands. However, other color mapping schemes may be employed according to the present disclosure, in which case it may be necessary to consider all three layers of color R, G, and B (or HSV). The set of features and selection criteria may be adjusted, as appropriate, to address alternative color mapping schemes, as will be apparent to persons skilled in the art based on the detailed description provided herein. With reference to FIGS. 16 and 17, CpG island detection results are presented, wherein edge histograms are employed n spectrograms derived using color mapping.

Exemplary GA-SVM System and Method for Feature Selection and Classification

1. Input: DNA sequence of length M to the disclosed system/method:
   Parameters:
      N—STFT window size,
      q—overlap,
      p—viewing resolution (where M>>p>N)
2. Convert the input DNA sequence of size N into a binary indicator sequence;
3. Apply short term Fourier transform (STFM) to the binary indicator sequence and produce a frequency domain vector
4. Map the frequency domain vectors for A, T, C and G into a color space, e.g., RGB or HSV;
5. Apply edge detection to DNA spectral image using a conventional edge detection method (e.g., Sobel or Canny edge detector);
6. Compute horizontal and vertical histograms for red, green, blue components (or HSV components) separately by using edge projection. The histograms can also represent combined colors. For example, C and G can be combined and represented by a green component and A and T can be combined to represent a red component;
7. Evaluate and rank a set of prominent spectral features using a feature selection method using a support vector machine with genetic algorithm. Alternatively, a recursive feature elimination method and/or principal component analysis may be employed to find prominent features. For example, the following features can be used: 127 features (extracted from a DNA segment which is N bases long, where N can vary; in an exemplary embodiment, N is 200 bp long)
   Number of green pixels (1)
   Number of red pixels (1)
   Number of green edge pixels (1)
   Number of red edge pixels (1)
   Number of green edge pixels minus number of red edge pixels (1)
   Red edge histogram count along the frequency axis (61)
   Green edge histogram count along the frequency axis (61)
8. Design/implement a classifier using a subset of the top ranking features from the previous step. In an exemplary embodiment of the present disclosure, a support vector machine classifier is employed; however, alternative classifiers may be employed without departing from the spirit or scope of the present disclosure, e.g., neural network(s), self-organizing map (SOM) techniques/systems and other classifiers known in the machine learning literature may be employed. The classifier detects and classifies unknown input DNA sequences into sub-segments that have repetitive DNA structure(s) (e.g., CpG islands);

9. DNA segments that satisfy the evaluation criteria are marked as repetitive element(s) and the start and end positions are noted/recorded (e.g., CpG island).

A flowchart for the exemplary GA-SVM system/method for feature selection and classification, as described herein above, is presented in FIG. 18. As with the comparative histogram/fixed threshold processing systems and methods described above, the disclosed GA-SVM systems/methods are typically implemented through appropriate software/programming that is run/operated on an appropriate processing unit. The processing system may be free-standing, e.g., a personal computer, or associated with a network (intranet, extranet, distributed network that communicates across the Internet, etc.). The processing unit/system typically communicates with appropriate memory/storage, e.g., for purposes of accessing software/programming, databases that contain parameters and values associated with the disclosed systems/methods, and for storage (both short-term and long-term) of values/data/images generated through the disclosed systems/methods. The disclosed processing unit/system also typically communicates with one or more output systems for displaying and/or recording the values/data/images generated according to the present disclosure, e.g., printer(s), monitor(s), and the like. Thus, the disclosed systems and methods are susceptible to computer and/or processor-based implementations, as are known to persons skilled in the art.

The disclosed comparative histogram/fixed threshold and GA-SVM systems/methods have wide ranging applicability and utility. For example, repetitive DNA spectral analysis can be used for fast whole genome analysis and for identifying/finding significant patterns for long DNA sequences. Indeed, the identification of such patterns can be used for epigenomic analysis of DNA sequences, which is important and/or useful for studying and diagnosing cancer, aging and developmental disorders.

It is important to note that both supervised and unsupervised classifications can be performed without mapping the FFT result into a color space. Features can be extracted directly from the 4-transformed binary indicator sequences. In this case, instead of an RGB spectrogram image, the input is the FFT transformed binary indicator sequences. Normalization can be an optional step. The rest of the analysis is performed on a feature vectors consisting of the 4 transformed indicator sequences combined to represent a full vector—representing each DNA segment.

Systems/Methods for Creating Spectrovideo from Spectrograms

According to a further aspect of the present disclosure, systems and methods for creating spectrovideo from a spectrograms associated with a DNA sequence are disclosed. The frequency spectrum of a very long DNA sequence (e.g., a chromosome which might be 150 million bases long) cannot be fit into a single spectrogram frame at any desired resolution. Instead of looking at individual images, exemplary systems and methods of the present disclosure facilitate the creation of a continuous video from spectrograms. The disclosed spectrovideo essentially corresponds to "panning" across a genome or other DNA sequence of interest. With spectrovideo, visualization of the genome in a short amount of time and at a desired resolution is enabled. In addition, analysis of the spectrovideo provides full genome analysis and permits detection of changes in full length DNA patterns.

In contrast to a spectrogram of the same sequence, the disclosed spectrovideo provides more resolution of the same sequence.

As disclosed herein, the creation and use of spectrovideos offers numerous advantages and/or functionalities, including:
Continuous viewing of the entire genome, as opposed to saving and displaying individual spectrograms;
Time savings: spectral video is produced by stitching the DNA spectrograms together, whereas viewing of spectrograms one at a time is very time consuming;
Analysis of the continuous linear genomic patterns. At a low resolution, these patterns might extend beyond a single spectrogram.
Visualizing long sequences at a desired resolution and fine level of detail.
The ability to change the resolution as viewing of a spectrovideo progresses. For example, when an interesting pattern appears, the disclosed system/method facilitates an immediate "dive" into more detail for a particular subsequence.

The disclosed system/method for translating spectrograms into a spectrovideo may be implemented through software/computer programming. According to an exemplary embodiment of the present disclosure, software/programming is provided for operation on a processing unit/computer, such software being adapted to display the frequency spectrum of an entire DNA sequence (or desired portion thereof) by gradually panning the spectrogram window across the DNA sequence, e.g., from the 5' to the 3' end. An exemplary program/algorithm for effectuating the disclosed spectrovideo is described herein. Reference is also made to the flowchart set forth in FIG. 19 hereto.

Exemplary Algorithm/Program for Creating Spectrovideo (1) Input: DNA sequence of length M to disclosed system/method Parameters:
N—STFT window size,
q—window interval (N—window overlap),
p—viewing resolution (the width of the video image), and
v—speed of viewing, i.e., number of spectral image columns shifted per video frame (where M>>p>N).

(2) Initialize: s=1; r=1.

(3) Starting at position s, for a p-long segment or sub-sequence of the full DNA sequence;

(4) Starting at position r, convert an input DNA sequence of size N into a binary indicator sequence;

(5) Apply short term Fourier transform to a binary indicator sequence and produce a frequency domain vector;

(6) Map the frequency domain vectors for A, T, C and G into a color space, e.g., RGB or HSV color space;

(7) If (r−s+1)<p, visualize the result and move forward q nucleotides: r=r+q. Go to step 4.

(8) If no DNA spectral image previously shown, display the spectral image. r=r+q. Go to step 4.

(9) If (r−s+1)<p+vq, remove the first column from the spectral image and add the latest generated column at the end. r=r+q. Go to step 4.

(10) If (r−s+1)>=p+vq, display spectral image. s=s+vq. r=r+q.

(11) If (r+N−1)<=M, go to step 4.

(12) Adjust the speed of viewing v as per user request. Normal speed is one column shift per video frame.

With reference to FIG. 20, an exemplary image from a spectrovideo is set forth. As is readily apparent from the image of FIG. 20 (which suffers from being stagnant—not a moving image), the disclosed spectrovideo-related system and method offers significant advantages for the review and analysis of DNA sequences, e.g., both for known and unknown biomarker detection. Moreover, scene change detection methods may be employed with respect to a spectrovideo to find breaks in linear visual features. For each scene in a spectrovideo, statistical features may be extracted from the spectral domain. Furthermore, individual scenes from a full (or substantially complete) spectrovideo may be clustered using unsupervised clustering methods. Indeed, unsupervised video feature detection methods, as discussed in greater detail below, may be employed to identify and/or reveal genome-wide similarities at the spectral DNA level. Such analytic techniques can thus be employed for automatic DNA analysis, e.g., to find gene networks, important motifs, spectrally and structurally repetitive DNA elements, and other prominent DNA patterns.

Unsupervised Spectrogram and Spectrovideo Analysis

According to exemplary embodiments of the present disclosure, spectrograms may be employed for unsupervised exploration of gene regulatory elements and networks. Indeed, large scale spectrogram analysis to find important regulatory elements is contemplated according to the present disclosure. Unsupervised methods, such as hierarchical clustering, may be employed in order to determine the groups of most prevalent patterns.

The most frequent patterns throughout a genome can generally be identified/located without relying on linear dependency of nucleotide occurrence (i.e., simple statistical measures). Traditional methods in bioinformatics use multiple sequence alignment in order to find ultra-conserved segments. However, with spectral analysis, the systems and methods of the present disclosure may be employed to identify evolutionary and/or slowly varying changes, and not ultra—but mostly conserved elements, that have occurred in the genome.

Using large scale spectrogram analysis techniques, the systems and methods of the present disclosure facilitate scanning of the genome and focus on spectrally-conserved sequences—from the point of view of similar frequencies of occurring patterns. Rather than looking at linear nucleotide order, the disclosed systems/methods advantageously examine structural characteristics that may only be apparent from the spectral representation—and hardly discernible with sequence alignment. An advantage of the disclosed technique/approach is that the distribution of each repetitive spectral pattern within a single chromosome may be visualized, e.g., across entire chromosomes and genomes. Indeed, the disclosed analytic techniques may be applied across genomes to identify both known and novel patterns. Long repetitive elements, e.g., starting with a few hundred base pairs to a few hundred thousand base pairs, such as Alu, short hairpin structures (e.g., microRNAs), SINEs, LINEs, and CpG islands, can be effectively characterized in this manner. In addition, patterns at different resolutions can be shown: within 200 bp windows and within 100 Kbp long windows. This facilitates detection of new classes of repetitive elements. Before applying applicable algorithm(s), certain repeat elements may be masked, e.g., elements that are of no interest to the user.

An exemplary method/algorithm is described herein below:

Step 1. For input DNA sequence (e.g., a chromosome), generate spectrogram $S_1$ of length L (L is the number of nucleotides), with a STFT window W (where W<L), and the window overlap is V, where V<W.

Step 2. Move R nucleotides to the right and generate spectrogram $S_i$ until the end of the DNA sequence is reached.

Step 3. With all the spectrograms generated in steps 1 and 2, perform unsupervised image based clustering (.e.g., k-means clustering, hierarchical clustering). Exemplary similarity metrics for use according to the disclosed method/algorithm include any image-based similarity metric, e.g., the L1 metric that generates C clusters. The features for clustering can include: color, texture, specific objects that appear in the images: lines, squares, diagonals, etc.

Step 4. Find the largest cluster, take the cluster center, and perform search against a known genome resource to see the label class of the elements of this cluster. This can reveal the most repetitive elements on a particular chromosome.

Step 5. Select one of (a) or (b):
  (a) Randomly choose P spectrograms that are farthest from the cluster center and perform a class label search. Verify that they also belong to the same class.
  (b) Visualize for the user the spectrograms and the types of class labels of all elements in spectrogram set. If a spectrogram is in a cluster, where the center is known but the spectrogram that is further away from the cluster center is unknown, then designate novel element as the class label of cluster center and visualize the difference.

Step 6. Continue with the second largest cluster, and perform/repeat steps (5) and (6). Proceed with the next largest cluster until the cluster center—class label is unknown. Denote that K clusters have known labels and U clusters have unknown labels.

Step 7. For all the U clusters with unknown labels, with substantial cluster size (typically, at least half of the maximum number of elements in the largest cluster): find the prevalence of the pattern, statistical distribution within the same chromosome. Find statistical distribution across chromosomes.

Step 8. Increase V and go to step (1) with a given step size (e.g., step size=1), until V reaches half of W, then go to step (9).

Step 9. Increase W and go to step (1), with a given step size, until W reaches half of L, then go to step (10).

Step 10. Increase L and go to step (1).

Step 11. Summarize results at each level of V, W, and L.

As will be readily apparent to persons skilled in the art, the disclosed method/algorithm may be adapted for computer-based operation/implementation, thereby facilitating automated operation thereof. Indeed, the disclosed method/algorithm may be advantageously performed in an unsupervised manner, thereby generating V, W and L values for DNA sequences without user supervision and/or intervention.

According to the present disclosure, novel elements by association may be identified using step 5, i.e., the disclosed method/algorithm facilitates identification of sequences having a potential significant similarity that had previously been unrecognized and/or unappreciated. Indeed, sequences from a first species can be efficiently and effectively compared against sequenced genomes from different species to determine and/or identify potentially novel elements within the DNA sequence for such species. In addition, novel classes of elements may be identified from DNA sequences by the techniques identified in step 7 of the foregoing method/algorithm. These classes can be efficiently and effectively explored against other genomes according to the present disclosure. Further applications of the disclosed method/algorithm include:

Intragenome comparison: An algorithm for large scale analysis can be applied to each chromosome of a studied genome. Then, all the cluster centers can be used to perform overall clustering to see functionally important elements (across chromosomes) for that genome.

Comparative genomics: An algorithm for large scale analysis can be applied to each genome of the known 200+ sequenced genomes. Then, all the cluster centers can be used to perform overall clustering to see functionally conserved elements during the evolution.

Spectrovideo Analysis to Find Genome-Wide Patterns

In further exemplary embodiments and implementations of the present disclosure, scene change detection methods may be applied to a spectrovideo generated according tot the techniques described above to find breaks in important linear visual features. For each scene, statistical features from the spectral domain can be extracted. Furthermore, individual scenes of the full spectrovideo can be clustered using unsupervised clustering methods. Unsupervised video feature detection methods can then be employed to reveal genome-wide similarities at the spectral DNA level. The results of such unsupervised detection methods can then be used for automatic DNA analysis in order to find gene networks, important motifs, repetitive DNA elements and other prominent DNA patterns. An exemplary methodology/algorithm for undertaking such unsupervised detection is described herein below:

Step 1. Generate spectrovideo for a given DNA sequence (e.g., a part or full chromosome);

Step 2. Extract features, e.g., horizontal and vertical edge histograms for a given window, color, length of edges, number of same colors on a particular column, etc.

Step 3. Find spectro-cuts, e.g., find continuous patterns using the extracted Features—this technique is similar to finding "cuts" in film.

Step 4. Cluster scenes, e.g., store the features for each spectro-cut. Indeed, spectro-cuts may be clustered using these features, as if clustering scenes in a video.

Step 5. Find clusters with longest elements, e.g., sort order and visualize "scenes" with particular length.

Step 6. Query spectral elements of the same length, e.g., the ones that belong to a single scene. Each segment corresponding to a spectro-cut may be advantageously checked against a known genomic resource (e.g., NCBI) to determine any known functional importance.

Thus, the systems, methods and techniques disclosed herein provide a series of valuable tools in assessing, determining and/or identifying repetitive patterns in DNA sequences, and for associating biologic and/or clinical significance to such patterns. Although the systems, methods and techniques have been described with reference to exemplary embodiments thereof, it is to be understood that the present disclosure is not limited to such exemplary embodiments. Rather, as will be readily apparent to persons skilled in the art, the disclosed systems, methods and techniques are susceptible to wide ranging variations, modifications and/or enhancements, without departing from either the spirit or scope of the present disclosure. The present disclosure expressly encompasses such variations, modifications and/or enhancements within the scope hereof.

The invention claimed is:

1. A method for assessing the presence of a notable region in a DNA sequence, comprising:
   a. providing a DNA sequence;
   b. creating a plurality of spectrograms based on the DNA sequence;
   c. performing at least one of the following functions with respect to the plurality of spectrograms: (i) creation of a spectrovideo, (ii) comparative histogram analysis, (iii) feature selection and classification, and (iv) unsupervised classification and discovery of structurally novel DNA elements.

2. A method according to claim 1, wherein the DNA sequence represents a genome, a chromosome or a portion thereof.

3. A method according to claim 1, wherein creation of the plurality of spectrograms includes: (i) input of the DNA sequence, (ii) conversion of the DNA sequence into a binary indicator sequence, (iii) application of a short term Fourier transform to the binary indicator sequence to produce frequency domain vectors, (iv) mapping of the frequency domain vectors into a color space to produce a DNA spectral image, (v) application of edge detection to a DNA spectral image; and (vi) computation of horizontal and vertical histograms of the DNA spectral image based on results of the edge detection.

4. A method according to claim 1, wherein the spectrovideo is created, and wherein creation of the spectrovideo involves an algorithm that runs on a processing unit.

5. A method according to claim 4, wherein the algorithm includes:
   (a) Inputting the DNA sequence of length M; Parameters: N-STFT window size, q-window interval (N-window overlap), p-viewing resolution (a width of the video image), and v-speed of viewing, which is a number of spectral image columns shifted per video frame (where $M >> p > N$);
   (b) Initializing $s=1$; $r=1$;
   (c) Starting at position s, for a p-long segment or subsequence of the full DNA sequence;
   (d) Starting at position r, converting a portion of the input DNA sequence of size N into a binary indicator sequence;
   (e) Applying a short term Fourier transform to the binary indicator sequence and producing frequency domain vectors;
   (f) Mapping the frequency domain vectors for A, T, C and G into a color space to produce a DNA spectral image;
   (g) If $(r-s+1)<p$, visualizing the result and moving forward q nucleotides: $r=r+q$, and going to step (d);
   (h) If no DNA spectral image has been previously shown, displaying the DNA spectral image, $r=r+q$, and going to step (d);
   (i) If $(r-s+1)<p+vq$, removing the first column from the DNA spectral image and adding the latest generated column at the end, $r=r+q$, and going to step (d);
   (j) If $(r-s+1)>=p+vq$, displaying the DNA spectral image, $s=s+vq$, and $r=r+q$;
   (k) If $(r+N-1)<=M$, going to step (d);
   (l) Adjusting the speed of viewing v as per user request; where a normal speed is one column shift per video frame.

6. A method according to claim 1, wherein the comparative histogram analysis is performed, and includes:
   (a) Inputting the DNA sequence of length M; Parameters: N-STFT window size, q-overlap, P-viewing resolution (where $M >> p > N$);
   (b) Converting a portion of the input DNA sequence of size N into a binary indicator sequence;
   (c) Applying a short term Fourier transform (STFM) to the binary indicator sequence and producing frequency domain vectors;
   (d) Mapping the frequency domain vectors for A, T, C and G into a color space to produce a DNA spectral image;
   (e) Applying edge detection to the DNA spectral image;
   (f) Computing horizontal and vertical histogram data for color components of the DNA spectral image by using edge projection;

(g) Evaluating the histogram data according to feature extraction criteria;
(h) Marking DNA segments that satisfy the feature extraction criteria as repetitive elements, and recording a start and an end position of each marked DNA segment.

7. A method according to claim 1, wherein feature selection and classification is performed, and includes:
   (a) Inputting the DNA sequence of length M; Parameters: N-STFT window size, q-overlap, P-viewing resolution (where M>>p>N)'
   (b) Converting a portion of the input DNA sequence of size N into a binary indicator sequence;
   (c) Applying a short term Fourier transform (STFM) to the binary indicator sequence and producing frequency domain vectors;
   (d) Mapping the frequency domain vectors for A, T, C and G into a color space to produce a DNA spectral image;
   (e) Applying edge detection to the DNA spectral image;
   (f) Computing horizontal and vertical histogram data for color components of the DNA spectral image by using edge projection;
   (g) Evaluating and ranking a set of spectral features of the DNA spectral image using the histogram data and a feature selection method that employs at least one of: (1) a support vector machine with a genetic algorithm; (2) a recursive feature elimination method; and (3) a principal component analysis;
   (h) Implementing a classifier using a subset of top ranking spectral features to classify DNA segments that have repetitive DNA elements;
   (i) Marking the classified DNA segments as repetitive elements, and recording start and end positions of the marked DNA segments.

8. A method according to claim 1, further comprising performing the unsupervised classification and discovery of structurally novel DNA elements within the DNA sequence.

9. A method according to claim 8, wherein the unsupervised classification and discovery of structurally novel DNA elements within the DNA sequence includes performing a clustering technique.

10. A method according to claim 8, wherein the unsupervised classification and discovery of structurally novel DNA elements within the DNA sequence includes performing the following steps:
   Step 1: For the input DNA sequence, generate a spectrogram $S_1$ of length L (L is the number of nucleotides), with a STFT window W (where W<L), and wherein a window overlap is V, where V<W;
   Step 2: Move R nucleotides to the right and generate spectrogram $S_i$, and repeat until the end of the DNA sequence is reached;
   Step 3: With all the spectrograms generated in steps 1 and 2, perform unsupervised image based clustering using at least one of the following features: color, texture, and specific objects that appear in the spectrograms;
   Step 4: Find and select a largest cluster and ascertain a center of the selected cluster;
   Step 5: Perform a search of the selected cluster against a known genome resource to ascertain a label class of the elements of the selected cluster by performing one of (a) or (b): (a) Randomly choosing P spectrograms that are farthest from the center of the selected cluster and performing a class label search, and verifying that they also belong to the same class, (b) providing a visualization to an operator of the spectrograms and the types of class labels of all elements in the spectrogram set, and when a spectrogram is in a cluster, where the center is known but the spectrogram that is further away from the cluster center is unknown, then designating a novel element as a class label of the cluster center and providing to the operator a visualization of the difference;
   Step 6: Select the next largest cluster;
   Step 7: Repeat steps (5) and (6) until the cluster center-class label is unknown and denote that K clusters have known labels and U clusters have unknown labels;
   Step 8: For all of the U clusters with unknown labels, with substantial cluster size: find a prevalence of the pattern, a statistical distribution within the same chromosome, and a statistical distribution across chromosomes;
   Step 9: Increase V and go to step (1) with a given step size, until V reaches half of W, then go to step (10);
   Step 10: Increase W and go to step (1), with a given step size, until W reaches half of L, then go to step (10);
   Step 11: Increase L and go to step (1);
   Step 12: Summarize results at each level of V, W, and L.

11. A method according to claim 1, wherein one or more DNA patterns are identified.

12. A method according to claim 11, wherein the one or more DNA patterns includes at least one of a CpG island, one or more Alu repeats, one or more non-coding RNAs, one or more tandem repeats, and one or more satellite repeats.

13. A system comprising at least one processor programmed to perform the method of claim 1.

14. A method according to claim 1, further including:
   conversion of the DNA sequence into a binary indicator sequence; and
   application of a short term Fourier transform to the binary indicator sequence, wherein at least one of supervised and unsupervised classifications are performed without mapping a result of the Fourier transform into a color space.

15. A method according to claim 14, wherein at least one feature is extracted directly from the binary indicator sequences.

* * * * *